US010251573B2

(12) United States Patent
Ousdigian et al.

(10) Patent No.: US 10,251,573 B2
(45) Date of Patent: Apr. 9, 2019

(54) ELECTROGRAM SUMMARY

(71) Applicant: Medtronic, Inc., Minneapolis, MN (US)

(72) Inventors: Kevin T Ousdigian, Shoreview, MN (US); Joel R Lauer, Rogers, MN (US); Adam C Richardson, Litchfield, MN (US)

(73) Assignee: Medtronic, Inc., Minneapolis, MN (US)

( * ) Notice: Subject to any disclaimer, the term of this patent is extended or adjusted under 35 U.S.C. 154(b) by 193 days.

(21) Appl. No.: 14/187,695

(22) Filed: Feb. 24, 2014

(65) Prior Publication Data

US 2014/0330147 A1    Nov. 6, 2014

Related U.S. Application Data

(60) Provisional application No. 61/818,974, filed on May 3, 2013.

(51) Int. Cl.
*A61B 5/04* (2006.01)
*A61B 5/044* (2006.01)
(Continued)

(52) U.S. Cl.
CPC .......... *A61B 5/04012* (2013.01); *A61B 5/044* (2013.01); *A61B 5/742* (2013.01); *A61N 1/37235* (2013.01); *A61B 5/046* (2013.01); *A61B 5/0452* (2013.01); *A61B 5/0464* (2013.01); *A61B 5/7282* (2013.01); *A61N 1/3622* (2013.01); *A61N 1/37247* (2013.01)

(58) Field of Classification Search
CPC ................ A61B 5/04012; A61B 5/044; A61B 5/0452–5/0472; A61B 5/7282; A61B 5/742; A61N 1/37247; A61N 1/37235
See application file for complete search history.

(56) References Cited

U.S. PATENT DOCUMENTS 5,716,384 A   2/1998  Snell
5,833,623 A   11/1998 Mann et al.
(Continued)

FOREIGN PATENT DOCUMENTS

WO   WO 2009/148428 A1   12/2009
WO   WO 2013/048980 A1   4/2013

OTHER PUBLICATIONS (PCT/US2014/036607) PCT Notification of Transmittal of the International Search Report and the Written Opinion of the International Searching Authority.

*Primary Examiner* — William J Levicky

(57) ABSTRACT

Example techniques, systems, and devices select one or more portions of EGM signal data for presentation based on an identified cardiac episode type of the EGM signal data. For example, one or more processors are configured to receive cardiac electrogram (EGM) signal data collected from a medical device associated with a patient. The EGM signal data may include a detected cardiac episode identified as one of a plurality of episode types. The one or more processors may also be configured to select, based on the identified one of the plurality of episode types, one or more portions of the EGM signal data associated with the detected cardiac episode, and output the selected one or more portions of the EGM signal data.

27 Claims, 18 Drawing Sheets

(51) Int. Cl.
  *A61B 5/00* (2006.01)
  *A61N 1/372* (2006.01)
  *A61B 5/046* (2006.01)
  *A61B 5/0464* (2006.01)
  *A61B 5/0452* (2006.01)
  *A61N 1/362* (2006.01)

(56) References Cited

U.S. PATENT DOCUMENTS

| | | |
|---|---|---|
| 5,954,666 A | 9/1999 | Snell |
| 6,161,039 A | 12/2000 | Krichen et al. |
| 6,473,638 B2 | 10/2002 | Ferek-Petric |
| 6,577,896 B2 | 6/2003 | Werner et al. |
| 6,583,796 B2 | 6/2003 | Jamar et al. |
| 6,599,250 B2 | 7/2003 | Webb et al. |
| 6,675,044 B2 | 1/2004 | Chen |
| 7,188,151 B2 | 3/2007 | Kumar et al. |
| 7,242,978 B2 * | 7/2007 | Cao ............... A61B 5/04525 600/509 |
| 7,831,301 B2 | 11/2010 | Webb et al. |
| 7,894,883 B2 | 2/2011 | Gunderson et al. |
| 8,073,536 B2 | 12/2011 | Gunderson et al. |
| 8,073,537 B2 | 12/2011 | Gunderson et al. |
| 8,224,431 B2 | 7/2012 | Drew |
| 8,401,644 B2 | 3/2013 | Gunderson et al. |
| 8,521,269 B1 | 8/2013 | Gunderson et al. |
| 8,521,281 B2 | 8/2013 | Patel et al. |
| 2004/0088374 A1 | 5/2004 | Webb et al. |
| 2007/0123788 A1 | 5/2007 | Gunderson et al. |
| 2007/0123790 A1 | 5/2007 | Gunderson et al. |
| 2007/0123941 A1 | 5/2007 | Gunderson et al. |
| 2008/0125824 A1 * | 5/2008 | Sauer ............... A61N 1/3622 607/14 |
| 2008/0270036 A1 | 10/2008 | Webb et al. |
| 2010/0106036 A1 * | 4/2010 | Dong ............... A61N 1/37247 600/523 |
| 2011/0077541 A1 * | 3/2011 | Dong ............... G06K 9/00536 600/515 |
| 2011/0112417 A1 | 5/2011 | Gunderson et al. |
| 2013/0079651 A1 | 3/2013 | Patel et al. |
| 2013/0079654 A1 | 3/2013 | Patel et al. |
| 2013/0085406 A1 * | 4/2013 | Gunderson ........... A61B 5/044 600/518 |
| 2013/0096445 A1 | 4/2013 | Patel |

* cited by examiner

ELECTROGRAM SUMMARY

CROSS-REFERENCE TO RELATED APPLICATIONS

This application claims the benefit of U.S. Provisional Application No. 61/818,974, filed on May 3, 2013. The disclosure of the above application is incorporated herein by reference in its entirety.

TECHNICAL FIELD

The invention relates to an electrogram (EGM) summary generated by an external computing device for presentation at a display device.

BACKGROUND

The capacity of various types of IMDs to collect and store large amounts of physiological data is increasing. Some IMDs implement pre-programmed algorithms to process collected physiological data to, for example, diagnose certain patient conditions and/or guide therapy delivered by the IMD. Some IMDs, such as implantable pacemaker-cardioverter-defibrillators, may implement algorithms to detect and classify cardiac arrhythmia episodes, in response to which the IMD may deliver therapy, such as a defibrillation shock.

IMDs may also implement one or more algorithms to monitor device integrity by, for example, tracking events characteristic of physiological sensing issues and/or device impedance changes. Certain components of implantable medical devices, like any other man-made device, are subject to fault or failure, for example, either due to operator error at the time of implant, or due to normal "wear and tear" on the components during the life of the device. These faults or failures can result in artifact signals which are sensed by the IMD and mistaken for physiological signals, thereby impacting the accuracy of the data analysis performed by the IMD in classifying episodes.

Many sophisticated data processing algorithms have been developed to perform more detailed analyses of data collected by IMDs. Some of these algorithms have been programmed on an external medical device that can be wirelessly coupled, for example, via telemetry, to an IMD for the transfer of the data from the IMD to the external device. Alternately, some of the algorithms have been programmed on computers, which are not wirelessly coupled to the device, and the data is transferred from external medical devices to the computers, for example personal or lap top computers, on a disk or via a network.

Such external algorithms can process the data received from IMDs to come to some conclusions regarding episode classification and events indicative of device integrity issues, and may further provide a presentation of the data in a format that allows a physician or clinician to further analyze the data. Such auxiliary analyses of data transferred from an IMD can allow a clinician to monitor patient condition, bring to light device integrity issues, and/or errors in one or more analyses performed by the IMD that have led to misclassification of episodes detected by the IMD. Such auxiliary analysis may thus help an attending physician or other clinician in making decisions to reposition or replace certain portions/components of the device due to faults or failures detected by the auxiliary analysis, and/or in making decisions related to re-programming of the implanted device in order to prevent misclassification errors in the future.

Methods employed by an algorithm for post processing of data associated with arrhythmic episodes, which are detected and classified by an implantable cardioverter defibrillator (ICD), are described in commonly assigned U.S. Pat. No. 7,894,883, entitled METHOD AND APPARATUS FOR POST-PROCESSING OF EPISODE DETECTED BY A MEDICAL DEVICE, incorporated herein by reference in its entirety. Examples of methods employed by algorithms that are tailored to identify and classify events indicative of a device integrity issue, in particular, faults or failures associated with lead components of the device, are described in commonly assigned U.S. Pat. No. 7,539,540, entitled TROUBLESHOOTING METHODS FOR A MEDICAL SYSTEM INCLUDING IMPLANTABLE COMPONENTS and in U.S. Pat. No. 7,047,083, entitled METHOD AND APPARATUS FOR IDENTIFYING LEAD-RELATED CONDITIONS USING LEAD IMPEDANCE MEASUREMENTS, which are each hereby incorporated by reference in their entireties.

SUMMARY

This disclosure generally describes techniques, systems, and devices, for creating an electrogram (EGM) summary with portions of EGM signal data selected based on the episode type of the detected cardiac episode included in the EGM signal. A computing device, e.g., a networked server or medical device programmer, may be configured to generate a condensed set of data (e.g., at least part of the EGM summary) that includes portions of the EGM signal data relevant for the type of cardiac episode detected during the time period during which the EGM signal data was collected from the patient. The selected portions of the EGM signal data may thus represent the detected cardiac episode through limited time segments of the entire EGM signal data collected during onset, detection, treatment, and/or termination of the detected cardiac episode.

Each episode type may be associated with a specific number of portions of EGM signal data to be included in the EGM summary. Each of these portions may be directed to various events such as the onset of the episode, medical device detection of the episode, one or more attempts at treatment of the episode, or termination of the episode (e.g., conversion to a normal rhythm). Each episode type may also specify the time duration for each portion. In some examples, one or more episode types may include episode subtypes. The episode may be classified as one of the episode subtypes, and the portions of the EGM signal data may be selected according to predetermined criteria associated with the classified episode subtype. The selected portions of EGM signal data may be truncated and/or combined to prevent duplicating any EGM signal data within the EGM summary. The EGM summary may be outputted and transmitted, via a network in some examples, to a computing device for display and review by a clinician.

In one example, the disclosure describes a method that includes receiving cardiac electrogram (EGM) signal data collected from a medical device associated with a patient, wherein the EGM signal data includes a detected cardiac episode identified as one of a plurality of episode types, selecting, by one or more processors and based on the identified one of the plurality of episode types, one or more portions of the EGM signal data associated with the detected cardiac episode, wherein each of the plurality of episode types are associated with respective selections of portions of the EGM signal data, and outputting the selected one or more portions of the EGM signal data as an episode summary of the detected cardiac episode.

In another example, the disclosure describes a system that includes one or more processors configured to receive cardiac electrogram (EGM) signal data collected from a medical device associated with a patient, wherein the EGM signal data includes a detected cardiac episode identified as one of a plurality of episode types, select, based on the identified one of the plurality of episode types, one or more portions of the EGM signal data associated with the detected cardiac episode, wherein each of the plurality of episode types are associated with respective selections of portions of the EGM signal data, and output the selected one or more portions of the EGM signal data as an episode summary of the detected cardiac episode.

In another example, the disclosure describes a computer-readable storage medium including instructions that, when executed, cause one or more processors to receive cardiac electrogram (EGM) signal data collected from a medical device associated with a patient, wherein the EGM signal data includes a detected cardiac episode identified as one of a plurality of episode types, select, based on the identified one of the plurality of episode types, one or more portions of the EGM signal data associated with the detected cardiac episode, wherein each of the plurality of episode types are associated with respective selections of portions of the EGM signal data, and output the selected one or more portions of the EGM signal data as an episode summary of the detected cardiac episode.

The details of one or more examples are set forth in the accompanying drawings and the description below. Other features, objects, and advantages will be apparent from the description and drawings, and from the claims.

DETAILED DESCRIPTION

Figure 1:
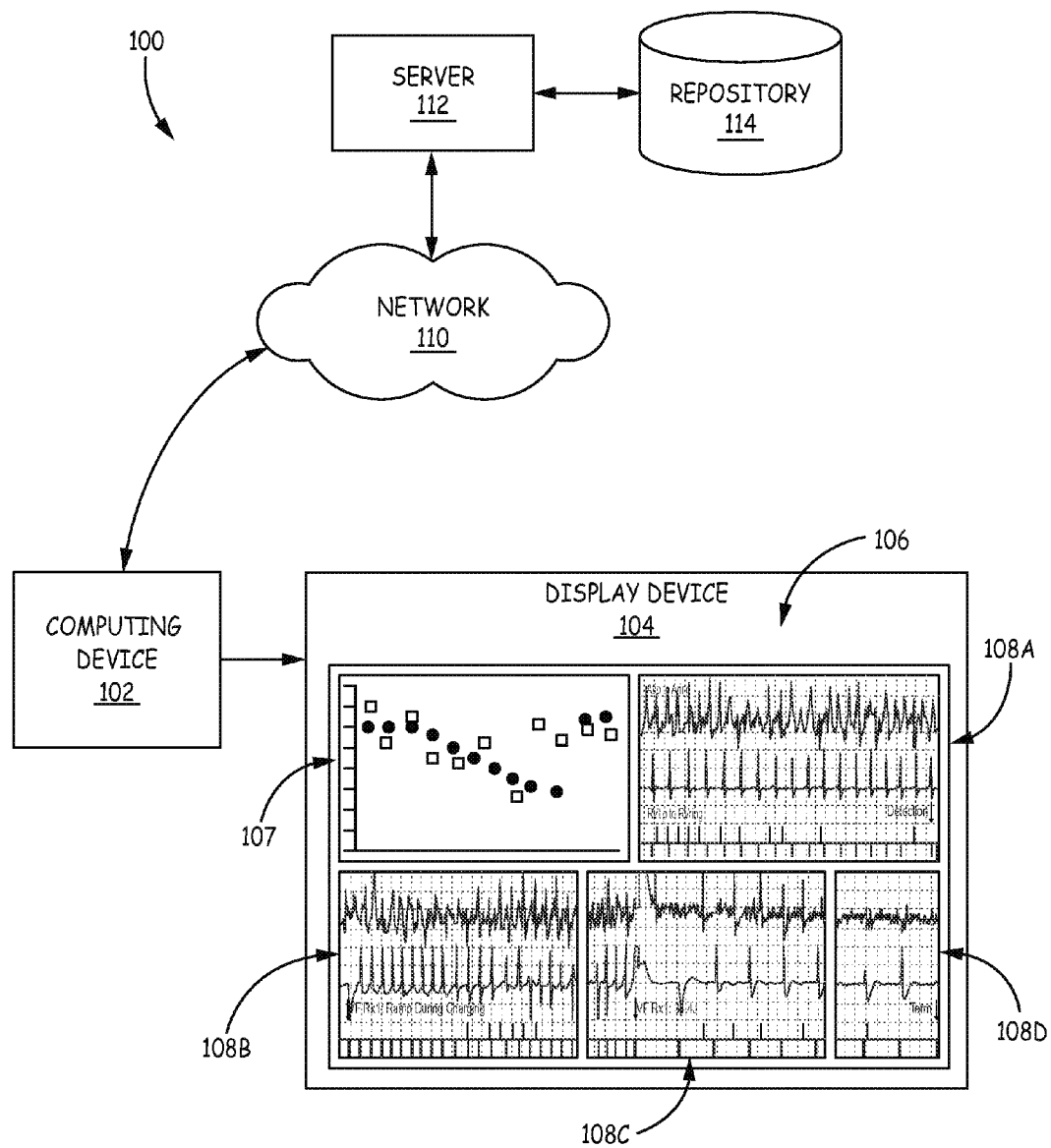
FIG. 1 is a conceptual drawing illustrating an example system configured to output an EGM summary including portions of EGM signal data selected based on an episode type of a detected cardiac episode, in accordance with one or more aspects of the disclosure.

This disclosure describes techniques, systems, and devices, for creating an electrogram (EGM) summary with selected portions of EGM signal data. Medical devices (e.g., implantable medical devices such as a pacemaker, cardioverter and/or defibrillator, or a monitor that does not provide therapy) may collect and store EGM signal data continuously or in response to detecting a cardiac episode such as a cardiac arrhythmia. The EGM signal data may be transmitted to an external device for storage and/or presentation to a clinician. For example, the programmer for the medical device may receive the EGM signal data and display the EGM signal data to the clinician for review. Alternatively, the EGM signal data may be transmitted to a remote computing device via a network for presentation to the clinician. The EGM signal data may be reviewed by the clinician to identify changing patient conditions, ineffective treatment, device malfunction, lead fractures, or any other issues that may be related to the monitoring or treatment of the patient.

However, the volume of EGM signal data to be reviewed by each clinician may be very large. Each clinician may need to review the full EGM signal data for dozens or hundreds of detected cardiac episodes for each patient. The clinician may have to sift through extensive EGM signal data, and many pages of patient data in some cases, for each episode of long durations. This review process may require a substantial investment of time for each patient. The extensive review of data may also increase the possibility that the clinician does not focus on important portions of the EGM signal data, limit the amount of time each clinician has to evaluate the patient, and/or limit the number of patients the clinician can evaluate each day.

As described herein, an EGM summary may be generated and transmitted for display (e.g., at a display device and/or printed to paper) to provide relevant portions (e.g., snippets or small time periods) of the EGM signal data for each detected cardiac episode. The EGM signal data to be included in the EGM summary may be limited to a predetermined time period or length of signal data (e.g., a predetermined number of seconds of data). In this manner, the EGM summary may be a concise representation of the detected cardiac episode with portions of the EGM signal data selected to convey respective events (e.g., onset of the episode, medical device detection of the episode, one or more delivered therapies, or termination of the episode) within the episode that are of interest to a clinician.

A computing device, e.g., a networked server or medical device programmer, may be configured to generate the condensed set of data (e.g., at least part of the EGM summary) that includes portions of the EGM signal data relevant for one of a plurality of cardiac episode types detected during the time period during which the EGM signal data was collected from the patient. The selected portions of the EGM signal data may thus represent the detected cardiac episode through limited time segments of the entire EGM signal data collected during onset, detection, treatment, and/or termination of the detected cardiac episode.

Each episode type may be associated with a specific number of portions of EGM signal data to be included in the EGM summary. Each of these portions may be directed to various events such as the onset of the episode, medical device detection of the episode, one or more attempts at treatment of the episode, or termination of the episode (e.g., conversion to a normal rhythm). Each episode type may also specify the time duration for each portion. In other words, different portions of EGM signal data may be relevant to different cardiac episode types. Example episode types include a treated ventricular tachycardia/ventricular fibrillation (VT/VF) episode, a monitored VT episode, a non-sustained ventricular tachycardia (VTNS) episode, a high-rate VTNS episode, a VT/VF episode with treatment withheld, a supraventricular tachycardia (SVT) episode, a ventricular oversensing (VOS) episode, a fast atrial and ventricular rate episode, a treated atrial tachycardia/atrial fibrillation (AT/AF) episode, and a monitored AT/AF episode.

In some examples, one or more episode types may include episode subtypes. The computing device may be configured to classify the detected cardiac episode as one of the episode subtypes, and the portions of the EGM signal data may be selected according to predetermined criteria associated with the classified episode subtype. In this manner, the computing device may select one or more portions of the EGM signal data based on characteristics of the episode and/or events that occurred during the episode. The computing device may also truncate or combine the selected portions of EGM signal data to prevent duplicating any EGM signal data within the EGM summary. The computing device may then output and transmit, via a network in some examples, the EGM summary to another computing device for display and review by a clinician.

FIG. 1 is a conceptual drawing illustrating example system 100 configured to output EGM summary 106 including portions of EGM signal data selected based on an episode type of a detected cardiac episode. As shown in FIG. 1, system 100 includes computing device 102, display device 104, network 110, networked server 112 (e.g., a computing device), and repository 114. Computing device 102, in some examples, is or is a part of a portable computing device (e.g., a mobile phone, a smartphone, a netbook computer, a notebook computer, a tablet computing device, or a smart watch). In other examples, computing device 102 may be at least a part of a workstation or other non-portable computing device. Computing device 102 may also be configured to control display device 104. Display device 104 may be housed by computing device 102 or external from computing device 102.

Computing device 102 may be configured to connect to network 110 (e.g., a wired or wireless network). In some examples, computing device 102 may also be configured to communicate with networked server 112 via network 110 to request and/or receive patient reports and/or EGM summaries within patient reports. Although network 110 may be a single network, network 110 may be representative of two or more networks configured to provide network access to server 112 and/or repository 114.

Computing device 102 may include various components that provide respective functionality. For example, computing device 102 may control display device 104. Computing device 102 may include display device 104 or display device 104 may separate from computing device 102. Computing device 102 may include one or more input devices and/or output devices that facilitate user (e.g., a clinician) communication with computing device 102. In one example, a user interface may include display device 104 and separate input devices or display device 104 may be touch screen interface (e.g., a presence-sensitive display that includes a presence-sensitive input device). In other examples, display device 104 may include a display and one or more buttons, pads, joysticks, mice, tactile devices, or any other device capable of turning user actions into electrical signals that control computing device 102. In any example, the user clinician may interact with the display device or any other input devices to provide input prior to or during the processes described herein.

In the example of FIG. 1, computing device 102 may be described as a tablet computing device (e.g., a mobile computing device). However, in other examples, computing device 102 may be a personal digital assistant (PDA), a desktop computer, a laptop computer, a tablet computer, or another type of computing device. In some examples, computing device 102 may be a remote computing device at a clinic or other location remote from the patient. In other examples, computing device 102 may be a medical device programmer configured to control the operation of the medical device collecting EGM signal data from the patient.

Retrieval of EGM signal data from server 112 and/or repository 114, or transmission of data to such devices, may require a connection between computing device 102 and networked server 112 using network 110. Both computing device 102 and networked server 112 may connect to network 110. Network 110 may be embodied as one or more of the Internet, a wireless network, a wired network, a cellular network, or a fiber optic network. In other words, network 110 may be any data communication protocol or protocols that facilitate data transfer between two or more devices. Networked server 112 may also connect to repository 114 to store and/or retrieve EGM signal data received from medical devices, EGM summary rules, episode classification rules, or any other information related to the generation of an EGM summary from EGM signal data.

Networked server 112 and repository 114 may each include one or more servers or databases, respectively. In this manner, networked server 112 and repository 114 may be embodied as any hardware necessary to provide patient reports, EGM summaries, or any other information related to the EGM signal data to computing device 102 or any other computing device. Networked server 112 may include one or more servers, desktop computers, mainframes, minicomputers, or other computing devices capable of executing computer instructions and storing data. In some examples, functions attributable to networked server 112 herein may be attributed to respective different servers for respective functions. Repository 114 may include one or more memories, repositories, hard disks, or any other data storage device. In some examples, repository 114 may be included within networked server 112.

Repository 114 may be included in, or described as, cloud storage. In other words, EGM signal data, EGM summaries, patient reports, instructions, or any other such information may be stored in one or more locations in the cloud (e.g., one or more repositories 114). Networked server 112 may access the cloud and retrieve the appropriate data as necessary. In some examples, repository 114 may include Relational Database Management System (RDBMS) software. In one example, repository 114 may be a relational database and accessed using a Structured Query Language (SQL) interface that is well known in the art. Repository 114 may alternatively be stored on a separate networked computing device and accessed by networked server 112 through a network interface or system bus. Repository 114 may thus be an RDBMS, an Object Database Management System (ODBMS), Online Analytical Processing (OLAP) database, or any other suitable data management system.

System 100 may be used to generate and deliver an EGM summary 106 to a clinician. In one example, one or more processors of server 112 may be configured to receive cardiac electrogram (EGM) signal data collected from a medical device (e.g., an implantable medical device) associated with a patient. Server 112 may be configured to receive the EGM signal data from repository 114 or directly from a networked device associated with the medical device. The EGM signal data includes a detected cardiac episode identified as one of a plurality of episode types. Server 112 may then select, based on the identified one of the plurality of episode types, one or more portions of the EGM signal data associated with the detected cardiac episode. Each of the plurality of episode types may be associated with respective selections of portions of the EGM signal data. Server 112 may then output the selected one or more portions of the EGM signal data. The selected one or more portions of the EGM signal data may be outputted as EGM summary 106 (e.g., an episode summary) for display at display device 104. Alternatively, or in addition, server 112 may output EGM summary 106 to be printed on paper or in any other form of media.

As shown in FIG. 1, computing device 102 has received the selected portions of the EGM signal data as an EGM summary 106. Computing device 102 then controls display device 104 to display EGM summary 106. The selected portions of the EGM signal data may be shown as EGM portions 108A, 108B, 108C, and 108D (collectively "EGM portions 108"). In addition to EGM portions 108, EGM summary 106 may also include interval summary 107 that includes representations of atrial and ventricle contraction intervals during the duration of the EGM signal data of the detected episode. EGM summary 106 may be part of a patient report that includes several EGM summaries, one for each detected cardiac episode during a duration of time.

Figure 2:
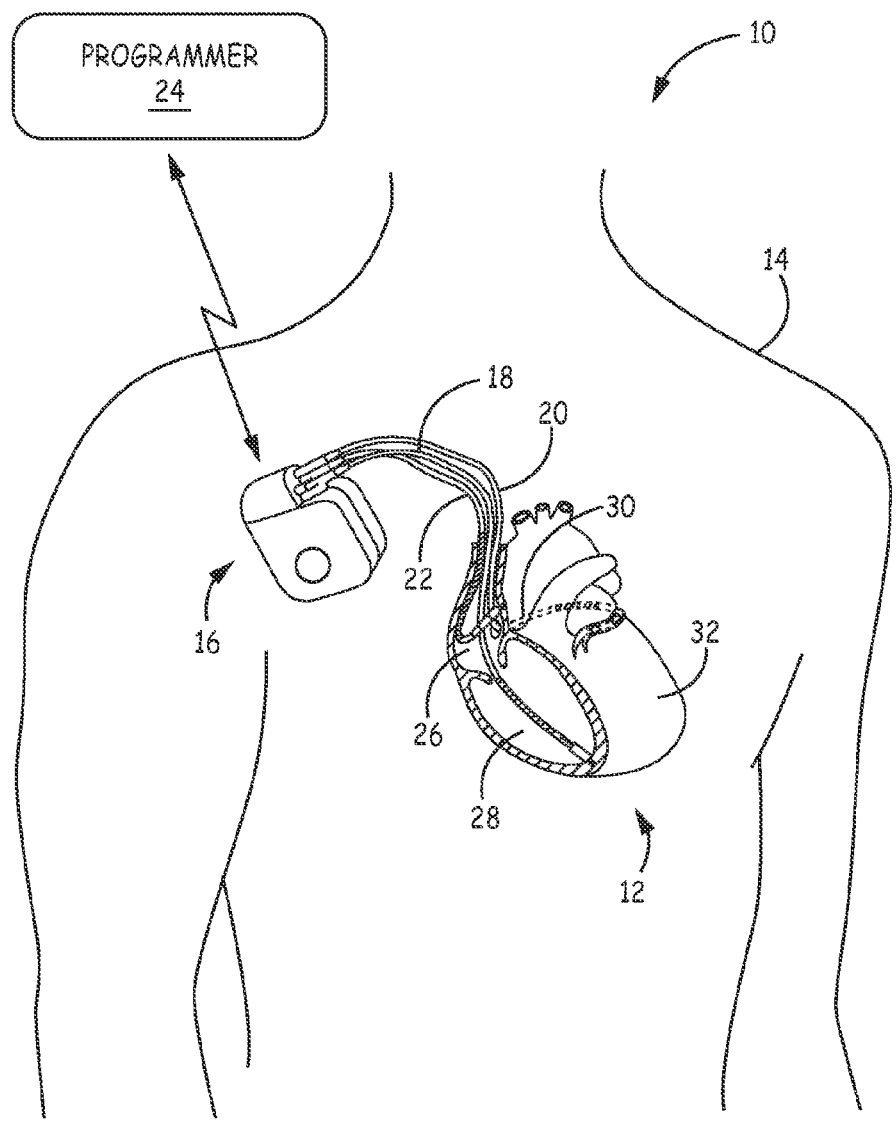
FIG. 2 is a conceptual drawing illustrating an example IMD and leads in conjunction with a heart.

The EGM signal data may have been originally obtained by a medical device associated with the patient, such as implanted medical device (IMD) 16 of FIG. 2. Server 112 may receive the EGM signal data periodically from the medical device and store it in repository 114 for later retrieval. Alternatively, server 112 may generate the EGM summary in response to receiving the EGM signal data. Each set of EGM signal data may be collected from the patient in response to the medical device detecting a cardiac episode such as an arrhythmia. Alternatively, the medical device may continuously collect EGM signal data and store the segment of EGM signal data that corresponds to the detected cardiac episode. In addition to the EGM signal data, the medical device may generate markers indicative of sensed heart beats and/or paced beats.

In some examples, the medical device may previously identify the detected cardiac episode included in the EGM signal data as one of a plurality of episode types. In other examples, server 112 may analyze the EGM signal data to identify, based on one or more signal characteristics, the episode type included in the EGM signal data. Signal characteristics may include frequency of sensed cardiac cycles, atrial-to-atrial (A-A) intervals, ventricular-to-ventricular (V-V) intervals, or any other distinguishing characteristics. Although the EGM signal data is described as including one cardiac episode, the cardiac episode may be a plurality of the same type of cardiac episode. In other words, a series of arrhythmic cardiac cycles may be referred to as a cardiac episode and identified as one type of episode.

The medical device and server 112 may recognize a plurality of different episode types (e.g., different types of arrhythmias). These episode types may include at least two of a treated ventricular tachycardia/ventricular fibrillation (VT/VF) episode, a monitored VT episode, a non-sustained ventricular tachycardia (VTNS) episode, a high-rate non-sustained ventricular tachycardia (VTNS) episode, a VT/VF episode with treatment withheld, a supraventricular tachycardia (SVT) episode, a ventricular oversensing (VOS) episode, a fast atrial and ventricular rate episode, a treated atrial tachycardia/atrial fibrillation (AT/AF) episode, and a monitored AT/AF episode.

The portions of the EGM signal data to be selected may be selected based on the identified episode type (e.g., determined according to rules for the identified episode type). In some examples, one or more of the different episode types may be associated with respective one or more episode subtypes. In other words, a first set of portions of the EGM signal data may be selected for one episode subtype of an episode type and a second set of portions of the EGM signal data may be selected for another episode subtype of the same episode type. In this manner, the different episode subtypes may be associated with respective selections of portions of the EGM signal data. These respective selections of portions may be different from each other.

Server 112 may be configured to classify the detected cardiac episode of the EGM signal data as one of the respective one or more episode subtypes of the episode type. Based on this classified episode subtype (e.g., in accordance with rules associated with the classified episode subtype), server 112 may select the one or more portions of the EGM signal data. These subtypes of episodes may provide more relevant portions, or snippets, of the EGM signal data for the specific events of the episode subtype.

Each of the selected portions of the EGM signal data may be determined by a respective time length for each portion with respect to an event within the EGM signal data. In this manner, server 112 may determine the time length of the respective portions of the EGM signal data based on the classified episode subtype. In addition, server 112 may be configured to determine the number of the portions of the EGM signal to be selected. This determined number may be based on the identified episode type and/or classified episode subtype.

Each determined portion may correspond to an event relevant to the episode type and subtype. For example, if detection, the first treatment, and termination events of the episode are applicable to the episode type, then server 112 may be instructed to select a portion of the EGM signal data that includes each of the events. In this manner, each selected portion of the EGM signal data is associated with a respective one or more events associated with the detected cardiac episode. Example events may include one or more of an onset of the cardiac episode, a medical device detection of the cardiac episode, a first delivered therapy, a last delivered therapy, and a termination of the cardiac episode.

In addition to selecting portions of the EGM signal data for EGM summary 106, server 112 may be configured to prevent any of the selected portions from including the same segment of EGM signal data, e.g., prevent different selected portions from including at least partially overlapping EGM signal data. In one example, server 112 may be configured to compare time windows for each of the plurality of portions of EGM signal data. The respective time windows may indicate a time duration during which the EGM signal data was collected from the patient. Server 112 may also determine that a first time window for a first one of the plurality of portions of EGM signal data overlaps with a second time window for a second one of the plurality of portions of EGM signal data. In other words, the portions would include the same segment of EGM signal data. In response to the determination, server 112 may truncate at least one of the first one of the plurality of portions of EGM signal data and the second one of the plurality of portions of EGM signal data to prevent the first one of the plurality of portions of EGM signal data from including EGM signal data from the same time as the second one of the plurality of portions of EGM signal data. Alternatively, server 112 may analyze the EGM signal data for the timing of one or more events (e.g., onset, detection, one or more therapies, and/or termination of the episode) to select non-overlapping portions of the EGM signal data.

In some examples, server 112 may combine the overlapping portions of the EGM signal data into a single timewise continuous portion of EGM signal data. For example, server 112 may combine portion 108B and 108C into a single continuous portion of EGM signal data. Server 112 may still label each portion of the EGM signal data even when presented in the single timewise continuous portion.

In addition to the selected portions of the EGM signal data, server 112 may generate additional information to be included into EGM summary 106. For example, server 112 may generate a timeline of markers, each of the markers indicating the occurrence of one of a respective sensed ventricular depolarization or a respective delivered pacing pulse. These markers may have been generated as part of a marker channel of the medical device. Server 112 may also generate, based on the EGM signal data, interval summary 107 indicating at least one of atrial contraction intervals and ventricle contraction intervals.

Server 112 may organize this information into EGM summary 106. For example, server 112 may organize portions 108 of the EGM signal data and interval summary 107 above the timeline of markers. Portions 108 of the EGM signal data may be matched to respective times of the timeline of markers, and interval summary 107 may be positioned above a portion of the time of markers corresponding to onset of the cardiac event when no EGM signal data is available for the onset event. Alternatively, interval summary 107 may be positioned prior in time to the onset portion of the EGM signal data. Server 112 may then output the organized, or generated, EGM signal data. Server 112 may also transmit EGM summary 106, alone or in combination with other EGM summaries, to computing device 102 via network 110.

Although only a single EGM summary 106 is shown in FIG. 1, multiple EGM summaries may be generated and grouped together into a patient report. The patient report may include multiple EGM summaries for a single episode type and/or EGM summaries for different episode types. In one example the patient report may only include EGM summaries for detected cardiac episodes that have occurred since the previous session. The session may be a session in which the clinician interrogated the programming device, the clinician last reviewed patient data, the clinician last met with the patient, or a change was made to the sensing or therapy from the medical device. In other examples, the patient report may include EGM summaries spanning multiple sessions. EGM summaries from prior sessions or EGM summaries that have been previously included in a patient report may be highlighted, surrounded by a different color border than EGM summaries of the current session, or otherwise include a visual indication of the time in which the EGM signal data was collected from the patient.

In some examples, EGM summary 106 (and a patient report) may be presented in an interactive form through which the clinician may make notes, request additional information, or otherwise modify the form or content of EGM summary 106. In response to receiving user input from the clinician, computing device 102 may perform the operation corresponding to the user input request and/or request server 112 to perform the operation and transmit the updated data back to computing device 102. In one example, EGM summary 106 may include a button that, when selected, causes computing device 102 to display the full EGM signal data corresponding to EGM summary. In other examples, EGM summary 106 (and the patient report) may not be interactive.

Although server 112 is generally disclosed as the computing device configured to select portions of the EGM signal data and/or generate EGM summary 106, different computing devices may perform these functions in other examples. For example, a medical device programmer (e.g., programmer 24 of FIG. 2) may select portions of EGM signal data based on the identified episode type for the EGM summary. In other examples, other computing devices, such as computing device 102, may perform the operations attributed to server 112. In still other examples, a medical device, such as IMD 16 of FIG. 2, may be configured to select portions of EGM signal data based on the identified episode type for the EGM summary.

FIG. 2 is a conceptual drawing illustrating example IMD 16 and leads in conjunction with heart 12. As illustrated in FIG. 2, an example system 10 for monitoring and treating cardiac episodes includes an implantable medical device (IMD) 16, such as an implantable cardiac pacemaker, implantable cardioverter/defibrillator (ICD), or pacemaker/cardioverter/defibrillator, for example. IMD 16 is connected to leads 18, 20 and 22 and is communicatively coupled to a programmer 24. IMD 16 senses electrical signals attendant to the depolarization and repolarization of heart 12, e.g., a cardiac electrogram (EGM), via electrodes on one or more leads 18, 20 and 22 or the housing of IMD 16. IMD 16 may also deliver therapy in the form of electrical signals to heart 12 via electrodes located on one or more leads 18, 20 and 22 or a housing of IMD 16, the therapy may be pacing, cardioversion and/or defibrillation pulses. IMD 16 may monitor EGM signals collected by electrodes on leads 18, 20 or 22, and based on the EGM signal detect and treat cardiac episodes. Programmer 24 may receive EGM signal data from IMD 16. The system for summarizing and displaying information regarding diagnosis and treatment may also be used with other medical devices, such as a cardiomyostimulator, a drug delivery system, cardiac and other physiological monitors, electrical stimulators including nerve, muscle and deep brain stimulators, cochlear implants and heart assist IMDs or pumps, for example.

Leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

In some examples, programmer 24 takes the form of a handheld computing device, computer workstation or networked computing device that includes a user interface for presenting information to and receiving input from a user. A user, such as a physician, technician, surgeon, electrophysiologist, or other clinician, may interact with programmer 24 to retrieve physiological or diagnostic information from IMD 16. Programmer 24 may provide to the user a summary of physiological and diagnostic information for patient 12 over a period of time. A user may also interact with programmer 24 to program IMD 16, e.g., select values for operational parameters of the IMD. Programmer 24 may include a processor configured to evaluate EGM signals transmitted from IMD 16 to programmer 24. In some examples, programmer 24 may evaluate a prior identification (e.g., classification) of a cardiac episode type by IMD 16.

IMD 16 and programmer 24 may communicate via wireless communication using any techniques known in the art. Examples of communication techniques may include, for example, low frequency or radiofrequency (RF) telemetry. Other techniques are also contemplated. In some examples, programmer 24 may include a programming head that may be placed proximate to the patient's body near the IMD 16 implant site in order to improve the quality or security of communication between IMD 16 and programmer 24. In some examples, programmer 24 may be located remotely from IMD 16, and communicate with IMD 16 via a network. Programmer 24 may also communicate with one or more other external devices using a number of known communication techniques, both wired and wireless.

In some examples, data acquired by IMD 16 can be monitored by an external system, which may comprise the programmer 24. The retrospective analysis of cardiac episodes according to an example of the present disclosure may take place in the programmer 24 once the required data is transmitted from IMD 16 to the programmer 24. In some examples, programmer 24 (or another device capable of communicating with IMD 16) may transmit the required data to another external device, such as server 112 of FIG. 1, for processing, analysis and/or presentation to a user. However, programmer 24 may perform the functions of server 112 in other examples.

The examples described herein are described with respect to cardiac episodes and EGM signal data indicative of cardiac events. However, the techniques described herein may be attributable to other electrograms, electrical signals, physiological data, sensed data, or any other data in which portions of the data may be selected based on detected episodes or events detected in the data.

Figure 3:
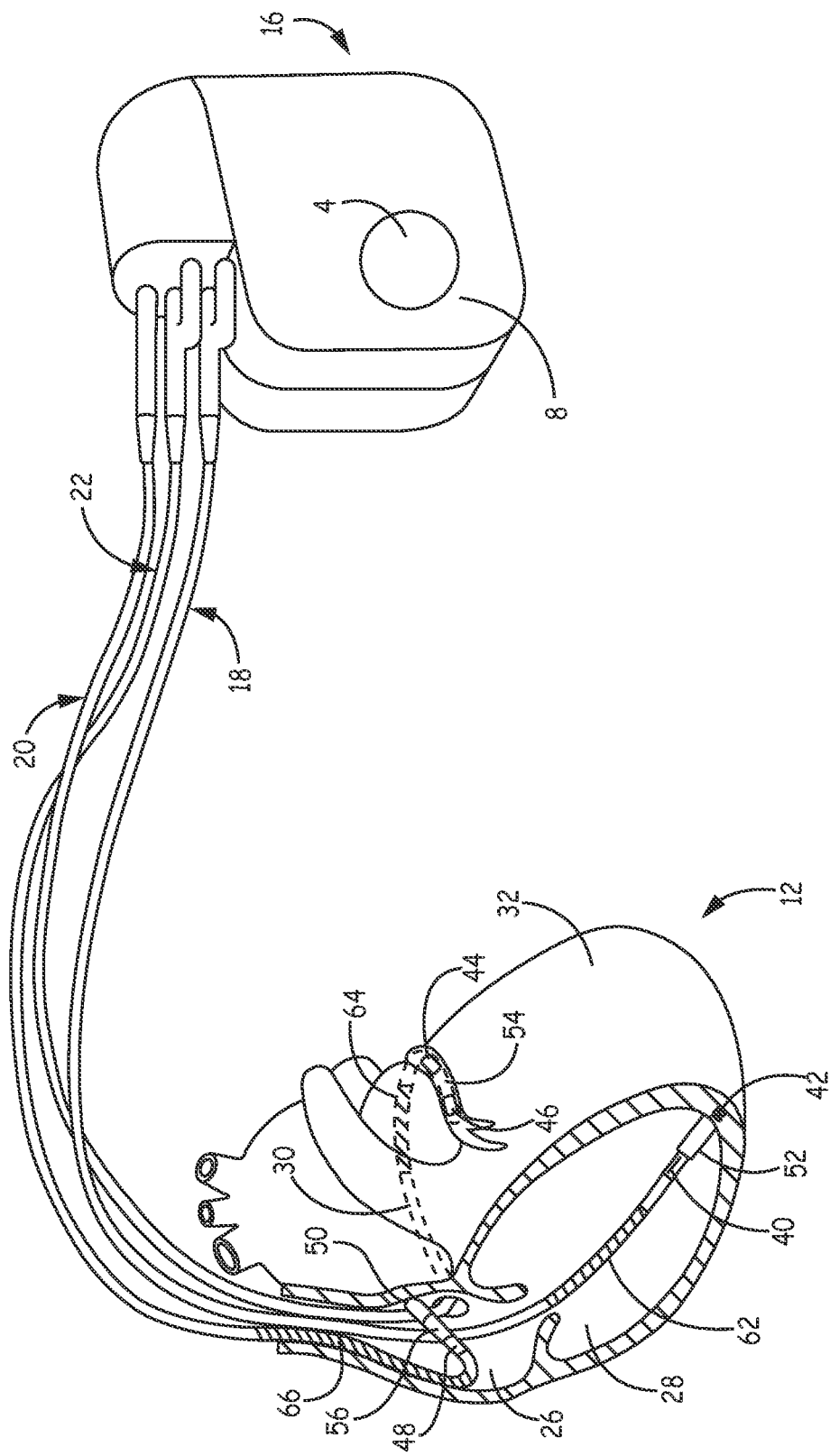
FIG. 3 is a conceptual drawing illustrating the example IMD of FIG. 2 coupled to a configuration of implantable medical leads in conjunction with a heart.

FIG. 3 is a conceptual drawing illustrating example IMD 16 of FIG. 2 coupled to a configuration of implantable medical leads 18, 20 and 22 of system 10 in conjunction with heart 12. In the illustrated example, bipolar electrodes 40 and 42 are located adjacent to a distal end of lead 18. In addition, bipolar electrodes 44 and 46 are located adjacent to a distal end of lead 20, and bipolar electrodes 48 and 50 are located adjacent to a distal end of lead 22. In alternative embodiments, not shown in FIG. 2, one or more of leads 18, 20 and 22, e.g., left-ventricular lead 20, may include quadrapole electrodes located adjacent to a distal end of the lead.

In the illustrated example, electrodes 40, 44 and 48 take the form of ring electrodes, and electrodes 42, 46 and 50 may take the form of extendable helix tip electrodes mounted retractably within insulative electrode heads 52, 54 and 56, respectively. Leads 18, 20, 22 also include elongated electrodes 62, 64, 66, respectively, which may take the form of a coil. In some examples, each of electrodes 40, 42, 44, 46, 48, 50, 62, 64 and 66 is electrically coupled to a respective conductor within the lead body of its associated lead 18, 20, 22 and thereby coupled to circuitry within IMD 16.

In some examples, IMD 16 includes one or more housing electrodes, such as housing electrode 4 illustrated in FIG. 2, which may be formed integrally with an outer surface of hermetically-sealed housing 8 of IMD 16, or otherwise coupled to housing 8. In some examples, housing electrode 4 is defined by an uninsulated portion of an outward facing portion of housing 8 of IMD 16. Other divisions between insulated and uninsulated portions of housing 8 may be employed to define two or more housing electrodes. In some examples, a housing electrode comprises substantially all of housing 8.

Housing 8 encloses a signal generator that generates therapeutic stimulation, such as cardiac pacing, cardioversion and defibrillation pulses, as well as a sensing module for sensing electrical signals attendant to the depolarization and repolarization of heart 12. Housing 8 may also enclose a memory for storing the sensed electrical signals. Housing 8 may also enclose a telemetry module for communication between IMD 16 and programmer 24.

IMD 16 senses electrical signals attendant to the depolarization and repolarization of heart 12 via electrodes 4, 40, 42, 44, 46, 48, 50, 62, 64 and 66. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 4.

The illustrated numbers and configurations of leads 18, 20 and 22 and electrodes are merely examples. Other configurations, i.e., number and position of leads and electrodes, are possible. In some examples, system 10 may include an additional lead or lead segment having one or more electrodes positioned at different locations in the cardiovascular system for sensing and/or delivering therapy to patient 14. For example, instead of or in addition to intercardiac leads 18, 20 and 22, system 10 may include one or more epicardial or subcutaneous leads not positioned within the heart.

Figure 4:
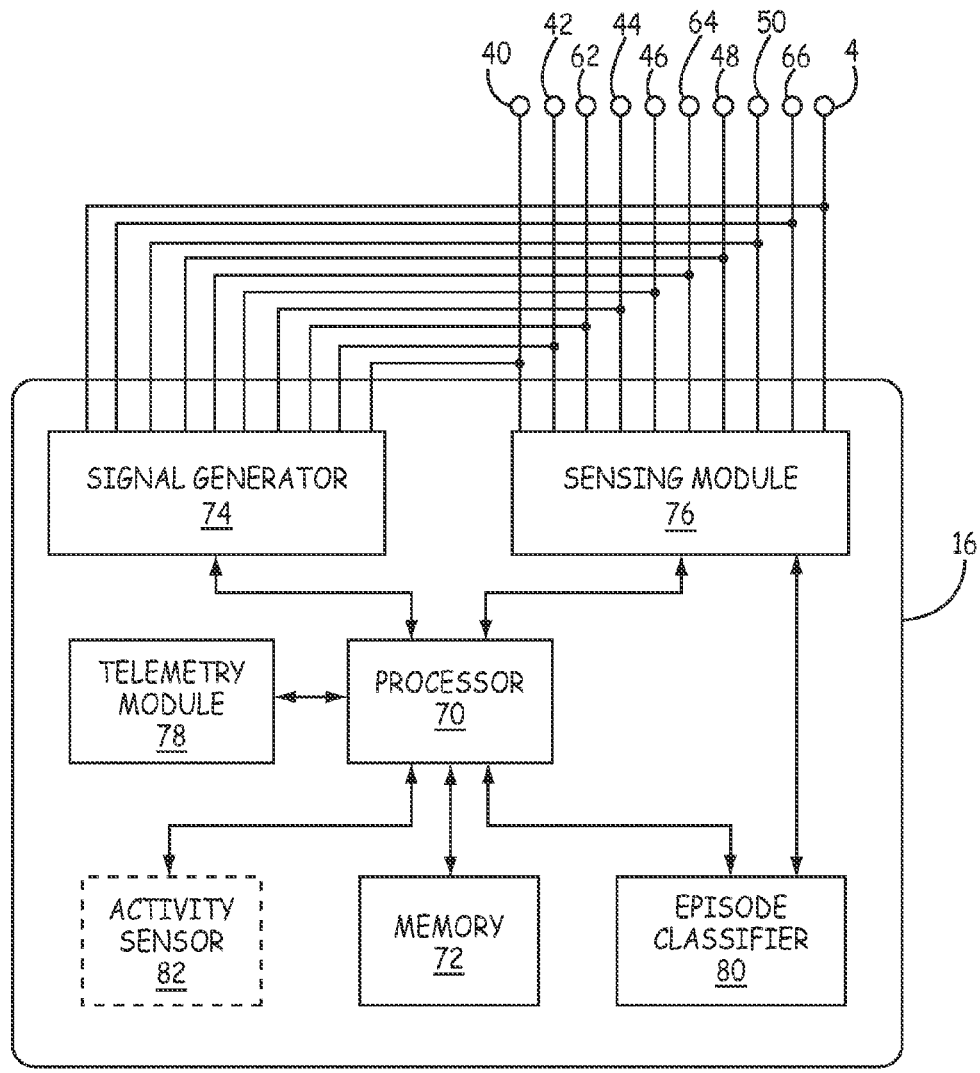
FIG. 4 is a functional block diagram illustrating an example configuration of the IMD of FIG. 2.

FIG. 4 is a functional block diagram illustrating an example configuration of IMD 16 of FIG. 3. IMD 16 may monitor and store EGM signals and classifies or identify abnormal signals before providing a therapeutic response. In the illustrated example, IMD 16 includes a processor 70, memory 72, signal generator 74, sensing module 76, telemetry module 78, episode classifier 80, and activity sensor 82. Memory 72 includes computer-readable instructions that, when executed by processor 70, cause IMD 16 and processor 70 to perform various functions attributed to IMD 16 and processor 70 herein. Memory 72 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 70 may include any one or more of a microprocessor, a controller, a digital signal processor (DSP), an application specific integrated circuit (ASIC), a field-programmable gate array (FPGA), or equivalent discrete or analog logic circuitry. In some examples, processor 70 may include multiple components, such as any combination of one or more microprocessors, one or more controllers, one or more DSPs, one or more ASICs, or one or more FPGAs, as well as other discrete or integrated logic circuitry. The functions attributed to processor 70 herein may be embodied as software, firmware, hardware or any combination thereof. Generally, processor 70 controls signal generator 74 to deliver stimulation therapy to heart 12 of patient 14 according to a selected one or more of therapy programs or parameters, which may be stored in memory 72. As an example, processor 70 may control signal generator 74 to deliver electrical pulses with amplitudes, pulse widths, frequency, or electrode polarities specified by the selected one or more therapy programs or parameters. Processor 70 may modify or initiate the electrical pulses delivered by signal generator 74 based on a detection or classification of an EGM signal by episode classifier 80.

Signal generator 74 is configured to generate and deliver electrical stimulation therapy to patient 14. As shown in FIG. 3, signal generator 74 is electrically coupled to electrodes 4, 40, 42, 44, 46, 48, 50, 62, 64 and 66, e.g., via conductors of the respective leads 18, 20, and 22 and, in the case of housing electrode 4, one or more conductors within housing 8. For example, signal generator 74 may deliver pacing, defibrillation or cardioversion pulses to heart 12 via at least two of electrodes 4, 40, 42, 44, 46, 48, 50, 62, 64 and 66. In some examples, signal generator 74 delivers stimulation in the form of signals other than pulses such as sine waves, square waves, or other substantially continuous time signals.

Signal generator 74 may include a switch module (not shown) and processor 70 may use the switch module to select, e.g., via a data/address bus, which of the available electrodes are used to deliver the electrical stimulation. The switch module may include a switch array, switch matrix, multiplexer, or any other type of switching device suitable to selectively couple stimulation energy to selected electrodes. Electrical sensing module 76 monitors electrical cardiac signals from any combination of electrodes 4, 40, 42, 44, 46 48, 50, 62, 64, and 66. Sensing module 76 may also include a switch module which processor 70 controls to select which of the available electrodes are used to sense the heart activity, depending upon which electrode combination is used in the current sensing configuration.

Sensing module 76 may include one or more detection channels, each of which may comprise an amplifier. The detection channels may be used to sense the cardiac signals. Some detection channels may detect events, such as R-waves or P-waves, and provide indications of the occurrences of such events to processor 70. One or more other detection channels may provide the signals to an analog-to-digital converter, for conversion into a digital signal for processing or analysis by processor 70 or episode classifier 80.

For example, sensing module 76 may comprise one or more narrow band channels, each of which may include a narrow band filtered sense-amplifier that compares the detected signal to a threshold. If the filtered and amplified signal is greater than the threshold, the narrow band channel indicates that a certain electrical cardiac event, e.g., depolarization, has occurred. Processor 70 then uses that detection in measuring frequencies of the sensed events.

In one example, at least one narrow band channel may include an R-wave or P-wave amplifier. In some examples, the R-wave and P-wave amplifiers may take the form of an automatic gain controlled amplifier that provides an adjustable sensing threshold as a function of the measured R-wave or P-wave amplitude. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety.

In some examples, sensing module 76 includes a wide band channel which may comprise an amplifier with a relatively wider pass band than the narrow band channels. Signals from the electrodes that are selected for coupling to the wide-band amplifier may be converted to multi-bit digital signals by an analog-to-digital converter (ADC) provided by, for example, sensing module 76 or processor 70. Processor 70 may analyze the digitized version of signals from the wide band channel. Processor 70 may employ digital signal analysis techniques to characterize the digitized signals from the wide band channel to, for example, detect and classify the patient's heart rhythm.

Processor 70 may detect and classify the patient's heart rhythm based on the cardiac electrical signals sensed by sensing module 76 employing any of the numerous signal processing methodologies known in the art. For example, processor 70 may maintain escape interval counters that may be reset upon sensing of R-waves by sensing module 76. The value of the count present in the escape interval counters when reset by sensed depolarizations may be used by processor 70 to measure the durations of R-R intervals, which are measurements that may be stored in memory 72. Processor 70 may use the count in the interval counters to detect a tachyarrhythmia, such as ventricular fibrillation or ventricular tachycardia. A portion of memory 72 may be configured as a plurality of recirculating buffers, capable of holding series of measured intervals, which may be analyzed by processor 70 to determine whether the patient's heart 12 is presently exhibiting atrial or ventricular tachyarrhythmia.

In some examples, processor 70 may determine that tachyarrhythmia has occurred by identification of shortened R-R interval lengths. Generally, processor 70 detects tachycardia when the interval length falls below 360 milliseconds (ms) and fibrillation when the interval length falls below 320 ms. These interval lengths are merely examples, and a user may define the interval lengths as desired, which may then be stored within memory 72. This interval length may need to be detected for a certain number of consecutive cycles, for a certain percentage of cycles within a running window, or a running average for a certain number of cardiac cycles, as examples.

In some examples, an arrhythmia detection method may include any suitable tachyarrhythmia detection algorithms. In one example, processor 70 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. and U.S. Pat. No. 5,755,736 to Gillberg et al. are incorporated herein by reference in their entireties. However, other arrhythmia detection methodologies may also be employed by processor 70 in some examples. For example, EGM morphology may be considered in addition to or instead of interval length for detecting tachyarrhythmias.

Generally, processor 70 detects a treatable tachyarrhythmia, such as VF, based on the EGM, e.g., the R-R intervals and/or morphology of the EGM, and selects a therapy to deliver to terminate the tachyarrhythmia, such as a defibrillation pulse of a specified magnitude. The detection of the tachyarrhythmia may include a number of phases or steps prior to delivery of the therapy, such as first phase, sometimes referred to as detection, in which a number of consecutive or proximate R-R intervals satisfies a first number of intervals to detect (NID) criterion, a second phase, sometimes referred to as confirmation, in which a number of consecutive or proximate R-R intervals satisfies a second, more restrictive NID criterion. Tachyarrhythmia detection may also include confirmation based on EGM morphology or other sensors subsequent to or during the second phase. Again, in some cases, processor 70 may mistakenly classify the patient's heart rhythm as a treatable tachyarrhythmia, e.g., as a result of a noisy EGM. In order to learn more about when IMD 16 is misclassifying patient's heart rhythms as shockable episodes, processor 70 may send a portion of an EGM signal that resulted in a classification of a treatable tachyarrhythmia.

IMD 16 also includes episode classifier 80. In some examples, classification or identification of a patient's heart rhythm based on an EGM signal from sensing module 76 occurs in episode classifier 80. Episode classifier 80 may employ any of the methods described herein for identifying an arrhythmia (e.g., a tachyarrhythmia) from an ongoing EGM signal. In some examples, episode classifier 80 stores a portion of the EGM signal within memory 72 on an ongoing basis. When an arrhythmia is not detected by the episode classifier, the EGM signal may be written over after a period of time. In response to a arrhythmia being detected, episode classifier 80 may direct memory 72 to store on a long term basis a time period or portion of the EGM signal leading up to the detection of the arrhythmia, along with the specific classification, e.g., VT, VF, or SVT. In some examples, detection may not result in stimulation being provided by IMD 16. The corresponding EGM signal may be categorized as non-sustained ventricular tachycardia (VTNS), AT, AF, monitored VT, or a ventricular oversensing (VOS) episode.

Although processor 70 and episode classifier 80 are illustrated as separate modules in FIG. 4, processor 70 and episode classifier 80 may be incorporated in a single processing unit. Episode classifier 80 may be a component of or a module, e.g., software module, executed by processor 70.

Activity sensor 82 may be optionally included in some examples of IMD 16. Activity sensor 82 may include one or more accelerometers. Information obtained from activity sensor 82 may be used to determine activity level or posture leading up to, or at the time of the abnormal heart rhythm. In some examples, this information may be used by IMD 16, e.g., episode classifier 80, to aid in the classification of an abnormal heart rhythm.

Activity sensor 82 may, for example, take the form of one or more accelerometers, or any other sensor known in the art for detecting activity, e.g., body movements or footfalls, or posture. In some examples, activity sensor 82 may comprise a three-axis accelerometer. Processor 70 may determine an activity level count at regular intervals based on the signal(s) from activity sensor 82. In some examples, processor 70 may determine a running average activity count based on the information provided by activity sensor 82. For example, the activity count may be calculated over a 1 second interval and the processor 70 may update the activity level count at a 1 second interval. A method of determining activity count from an accelerometer sensor is described in U.S. Pat. No. 6,449,508, to Sheldon et al, entitled, "ACCELEROMETER COUNT CALCULATION FOR ACTIVITY SIGNAL FOR AN IMPLANTABLE MEDICAL DEVICE," issued Sep. 10, 2002, and incorporated herein by reference in its entirety.

Activity sensor 82 may be located outside of the housing 8 of IMD 16. Activity sensor 82 may be located on a lead that is coupled to IMD 16 or may be implemented in a remote sensor that wirelessly communicates with IMD 16 via telemetry module 78 or another wireless communication medium. In any case, activity sensor 82 is electrically or wirelessly coupled to circuitry contained within housing 8 of IMD 16.

Telemetry module 78 includes any suitable hardware, firmware, software or any combination thereof for communicating with another device, such as programmer 24 (FIG. 1). Under the control of processor 70, telemetry module 78 may receive downlink telemetry from and send uplink telemetry to programmer 24 with the aid of an antenna, which may be internal and/or external. In some examples, processor 70 may transmit cardiac signals, e.g., ECG or EGM signal data, produced by sensing module 76 and/or signals selected by episode classifier 80 to programmer 24. Processor 70 may also generate and store marker codes indicative of different cardiac events (or other physiological events) detected by sensing module 76 or episode classifier 80, and transmit the marker codes (e.g., a timeline of markers) to programmer 24. An example IMD with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety. Information which processor 70 may transmit to programmer 24 via telemetry module 78 may also include an indication of a change in disease state of the heart, an indication of a change in heart response to the therapy provided or an indication that the heart continues to response in the same (or similar) manner to the therapy provided, the indications based on heart sounds and/or EGM signals. Such information may be included as part of a marker channel with an EGM.

Figure 5:
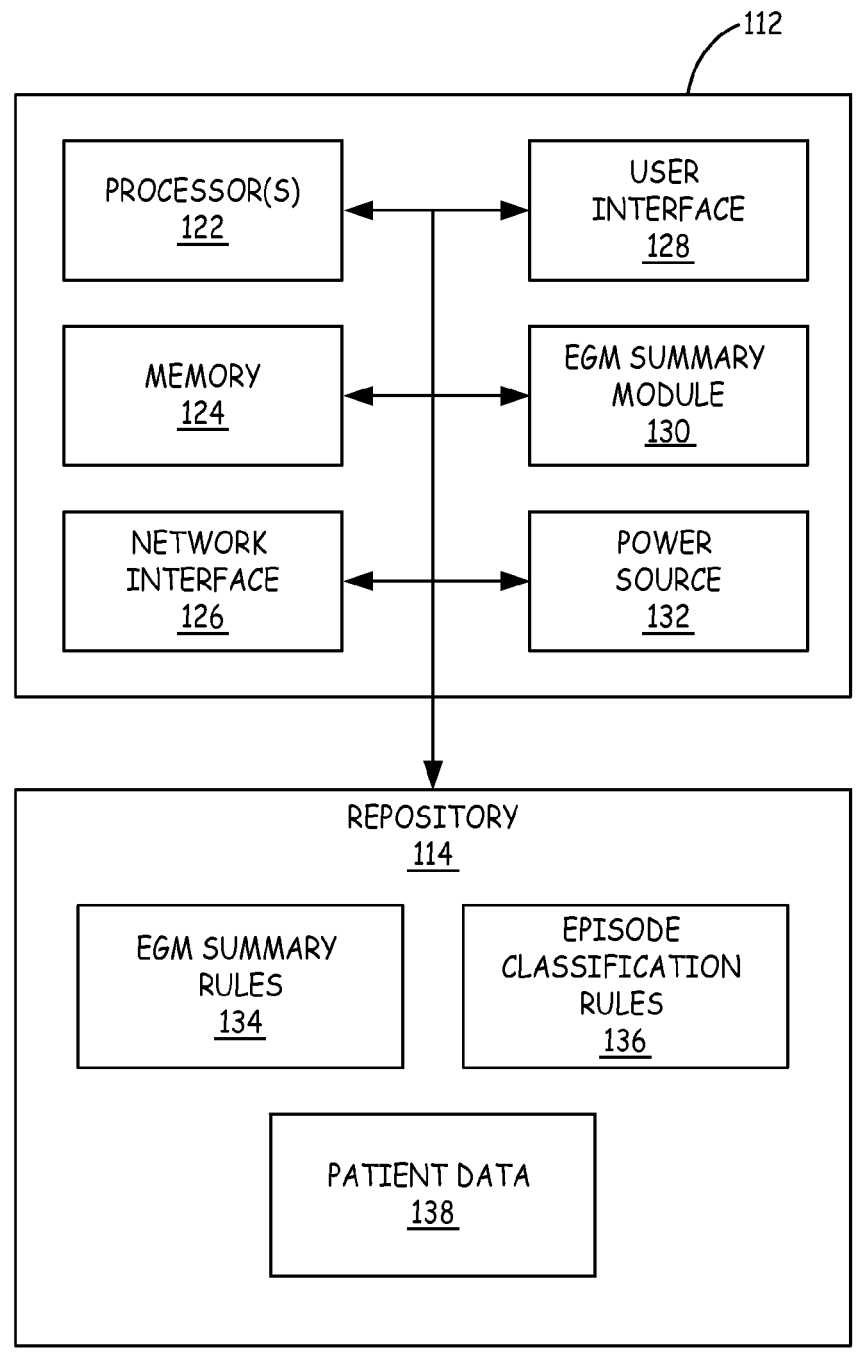
FIG. 5 is a functional block diagram illustrating an example configuration of the networked server and repository of FIG. 1.

FIG. 5 is a functional block diagram illustrating an example configuration of networked server 112 and repository 114 of FIG. 1. FIG. 5 illustrates only one particular example of server 112, and many other example embodiments of server 112 may be used in other instances. For example, server 112 may include additional components and run multiple different applications. Server 112 may be configured to generate EGM summaries, patient reports with one or more of the EGM summaries, identify or classify cardiac episodes, or any other functions described herein.

As shown in the specific example of FIG. 5, server 112 may include and/or house one or more processors 122, memory 124, a network interface 126, user interface 128, EGM summary module 130, and power source 132. Server 112 may be in communication with repository 114, such that repository 114 is located external of server 112. In other examples, repository 114 may include one or more storage devices within an enclosure of server 112. Server 112 may also include an operating system, which may include modules and/or applications that are executable by processors 122 and server 112. Each of components 122, 124, 126, 128, 130, 132, and 134 may be interconnected (physically, communicatively, and/or operatively) for inter-component communications.

Processors 122, in one example, are configured to implement functionality and/or process instructions for execution within server 112, such as selecting portions of EGM signal data, generating EGM summaries, and generating patient reports including the EGM summaries and/or other information related to a patient. For example, processors 122 may be capable of processing instructions stored in memory 124 or instructions stored in repository 114 (e.g., EGM summary rules 134 or episode classification rules 136). These instructions may define or otherwise control the operation of server 112.

Memory 124, in one example, is configured to store information within server 112 during operation. Memory 124, in some examples, is described as a computer-readable storage medium. Memory 124 may also be described as a storage device or computer-readable storage device. In some examples, memory 124 is a temporary memory, meaning that a primary purpose of memory 124 is not long-term storage. However, memory 124 may also be described as non-transitory. Memory 124, in some examples, may be described as a volatile memory, meaning that memory 124 does not maintain stored contents when the computer is turned off. Examples of volatile memories include random access memories (RAM), dynamic random access memories (DRAM), static random access memories (SRAM), and other forms of volatile memories known in the art. In some examples, memory 124 is used to store program instructions for execution by processors 122. Memory 124, in one example, is used by software or applications running on server 112 to temporarily store information during program execution. Although memory 124 of FIG. 5 is not described as including EGM summary rules 134, episode classification rules 136, and patient data 138, memory 124 may store such instructions and data in other examples.

Repository 114, in some examples, also includes one or more computer-readable storage media, such as one or more storage devices. Repository 114 may be configured to store larger amounts of information than memory 124. Repository 114 may further be configured for long-term storage of information. In some examples, repository 114 may include non-volatile storage elements. Examples of such non-volatile storage elements include magnetic hard discs, optical discs, floppy discs, flash memories, or forms of electrically programmable memories (EPROM) or electrically erasable and programmable (EEPROM) memories.

Repository 114 may be configured to store information related to or collected from each of multiple patients. This information may include patient information and/or patient data used to generate EGM summaries and patient reports as described herein. For example, repository 114 may store patient data 138, EGM summary rules 134, and episode classification rules 136. For each of patient data 138, EGM summary rules 134, and episode classification rules 136, repository 114 may maintain separate files for each patient or otherwise maintain security of the data to retain patient privacy.

Patient data 138 may include collected EGM signal data that may or may not include one or more detected cardiac episodes (e.g., tachyarrhymia episodes), marker history for sensed and paced heart beats, therapy delivery history, therapy parameters for respective patients, clinician annotations, or any other information that is related to one or more patients. Patient data 138 may include sensed or detected patient data obtained from one or more medical devices, such as IMD 16. Patient data 138 may include data from one or more patients. The data for each patient may be stored in separate files, for example.

EGM summary rules 134 may include instructions for selecting the one or more portions of each set of EGM signal data, how to organize the portions into the EGM summary for presentation, retrieving any additional information such as a timeline of markers for cardiac cycles, and how to generate a patient record with one or more EGM summaries. For example, each of the plurality of episode types may be associated with respective selections of portions of the EGM signal data. Each of the selections of portions may be different from each other, although some of the selections of portions may be identical for two or more of the episode types. Episode classification rules 136 may include instructions for server 112 to classify or identify each of the cardiac episode types and/or each of the episode subtypes for respective episode types from sets of EGM signal data. In some examples, at least part of episode classification rules 136 may also be stored by the medical device such that the medical device can detect the cardiac episodes. In some examples, various instructions of EGM summary rules 134 and episode classification rules 136 may be combined into different sets of instructions and/or separated into individual sets of instructions. The details of various EGM summary rules 134 and episode classification rules 136 will be described in detail below.

Server 112, in some examples, also includes a network interface 126. Server 112, in one example, utilizes network interface 126 to communicate with other computing devices (e.g., computing device 102 of FIG. 1), programmers (e.g., programmer 24 of FIG. 2), medical devices (e.g., IMD 16 of FIG. 2), or more networks, such as network 110 shown in FIG. 1. In this manner, server 112 may transmit and/or receive EGM signal data, selected portions of EGM signal data, EGM summaries, and/or patient reports. Network interface 126 may be a network interface card, such as an Ethernet card or other wired interface. In other examples, network interface 126 may include an optical transceiver, a radio frequency transceiver, or any other type of device that can send and receive information. Other examples of such network interfaces may include Bluetooth, 3G and WiFi radios in mobile computing devices as well as USB. In some examples, server 112 utilizes network interface 126 to wirelessly communicate with another computing device (e.g., computing device 166N of FIG. 7) or other networked computing devices.

Server 112, in one example, also includes one or more user interfaces 48. User interface 128 may include a touch-sensitive and/or a presence-sensitive screen, mouse, a keyboard, a voice responsive system, camera, or any other type of device for detecting a command from a user. In one example, user interface 128 may include a touch-sensitive screen, sound card, a video graphics adapter card, or any other type of device for converting a signal into an appropriate form understandable to humans or machines. In addition, user interface 128 may include a speaker, a cathode ray tube (CRT) monitor, a liquid crystal display (LCD), or any other type of device that can generate intelligible output to a user.

Server 112, in some examples, includes one or more power sources 132, which provide power to server 112. Generally, power source 132 may utilize power obtained from a wall receptacle or other alternating current source. However, in other examples, power source 132, may include one or more rechargeable or non-rechargeable batteries (e.g., constructed from nickel-cadmium, lithium-ion, or other suitable material). In other examples, power source 132 may be a power source capable of providing stored power or voltage from another power source.

Server 112 may, in some examples, utilize EGM summary module 130 to select portions of EGM signal data based on identified episode types and episode subtypes, organize the selected portions of EGM signal data into an EGM summary for each detected cardiac episode of each episode type, and generate a patient report with one or more EGM summaries. EGM summary module 130 may communicate with repository 114 to retrieve, in accordance with instructions such as stored commands or user input, EGM summary rules 134, episode classification rules 136, and/or patient data 138 as needed to generate the EGM summaries. In some examples, EGM summary module 130 may retrieve EGM signal data from a medical device or programmer in response to a request for an EGM summary or patient report. EGM summary module 130 may include dedicated hardware (e.g., one or more processors), firmware, and/or software to perform the functions described herein. In other examples, one or more of processors 122 may perform some or all of the functions described herein within respect to EGM summary module 130. Any software implemented within or executed by server 112 may be implemented or contained within, operable by, executed by, and/or be operatively/communicatively coupled to components of server 112 (e.g., processors 122, memory 124, network interface 126, and/or repository 114).

As described above, repository 114 may include various instructions for classifying or identifying cardiac episodes and generating EGM summaries. Episode classification rules 136 may include rules for classifying episode subtypes of one or more episodes. An episode type may be classified as two or more different subtypes according to various events associated with the episode such as the number and/or type of delivered therapies (e.g. a cardioversion shock or anti-tachycardia pacing (ATP)), the number and/or type of aborted therapies, or any other events or variations between different subtypes of the episode. Due to these different events that may occur during an episode of a particular episode type, different portions of the EGM signal data collected in association with the episode may be appropriate for the EGM summary of the episode. The classification of episode subtypes may thus be performed, according to the instructions of episode classification rules 136, in order for server 112 to select the portions of the EGM signal data relevant to briefly describe the episode via the EGM summary.

The episode type of each detected cardiac episode of respective sets of EGM signal data may be determined by the medical device (e.g., as the medical device is programmed to detect such cardiac episode and, in some cases, provide appropriate therapy). In examples for which the medical device did not identify the episode type or for confirmation purposes, server 112 may be configured to identify the episode type of each respective episode represented in the EGM signal data. Episode classification rules 136 may include rules to classify, or identify episode types in addition to episode subtypes. Although episode classification rules 136 are shown as separate from EGM summary rules 134, episode classification rules 136 may be linked to or included within EGM summary rules 134.

EGM summary rules 134 may include instructions, equations, look-up tables, or any other information from which server 112 may use to select one or more portions of respective EGM signal data to generate an EGM summary. Tables 1-9 below describe example episode types, episode subtypes, and the corresponding portions of EGM signal data to use for an EGM summary. Some episode types include multiple episode subtypes. Other episode types may be described has having zero subtypes or just one subtype. The episode types, episode subtypes, and portions of the EGM signal data are just one example of how to determine which portions to select. The example portions may be provided based on EGM Summary formatting options for particular display systems. Other portions, episodes, and episode types may be different in other examples. For example, EGM summary rules 134 may include additional episode subtypes for one or more episodes and/or different portions of the EGM signal data for each of the episode types/subtypes.

Tables 1-9, and other tables herein, include various terms to described events and segments of EGM signal data. The term "Detection" may describe the point of initial detection for the episode. The term "CD" may refer to the point where a cardioversion/defibrillation pulse (e.g., shock) occurred. The term "Last Shock" may refer to the last shock therapy stored for the episode, which may or may not be the last therapy delivered for the episode. The term "Aborted Shock" may refer to the point at which the first aborted shocked occurred. The term "ATP" may refer to the ventricular event when the ATP sequence started. The term "Last ATP" may refer to the ventricular event when the last ATP sequence started. The term "Duration" may refer to the difference in time as indicated by EGM signal data record for the specified points in the episode.

Table 1 provides an overview of the example portions of the EGM signal data to be selected for respective episode types. The episode types of Table 1 include a treated VT/VF episode, a monitored VT episode, a non-sustained ventricular tachycardia (VT-Non sustained) episode, a high-rate non-sustained ventricular tachycardia (VTNS) episode, a VT/VF episode with treatment withheld, a supraventricular tachycardia (SVT) episode, a ventricular oversensing (VOS) episode, a fast atrial and ventricular rate episode, a treated atrial tachycardia/atrial fibrillation (AT/AF) episode, and a monitored AT/AF episode. For each of these episode types, one or more portions of the corresponding EGM signal data is selected by server 112. Each of the plurality of episode types may be associated with respective selections of portions of a set of EGM signal data. Each of the selections of portions may be different from each other, although some of the selections of portions may be identical for two or more of the episode types. For example, the selection of portions may be the same for the episode types of monitored VT, VT-non sustained (VTNS), and high rate VTNS.

TABLE 1

| Episode Type | Portions | ICD | IPG |
|---|---|---|---|
| Treated VT/VF | Up to 6 sec EGM at detection with up to 6 sec markers prior to that (this is onset) EGM with first therapy EGM with last therapy (4.8 sec per therapy if 2 Therapies, 9.8 sec if one Therapy) 2 sec EGM at termination | X | |
| Monitored VT | Up to 6 sec EGM at detection with up to 6 sec markers prior to that | X | X |
| VT-Non sustained | Up to 6 sec EGM at termination with up to 6 sec markers prior to that | X | X |
| High Rate Non-sustained | Up to 6 sec EGM at termination with up to 6 sec markers prior to that | X | |
| VT/VF Therapy Withheld | Up to 6 sec EGM ending when detection is first withheld with up to 6 sec markers prior to that. Detection algorithm withholds VT/VF detection because it classifies the arrhythmia as SVT or Ventricular Oversensing | X | |
| Either SVT or Ventric- | Up to 6 sec EGM ending when detection is first withheld with up to 6 sec markers prior to that. Detection algorithm withholds VT/VF | X | |

TABLE 1-continued

| Episode Type | Portions | ICD | IPG |
|---|---|---|---|
| ular Over-sensing | detection because it classifies the arrhythmia as SVT or V. Oversensing | | |
| Fast A&V | Up to 6 sec EGM at detection with up to 6 sec markers prior to that | | X |
| Treated AT/AF | Up to 6 sec EGM ending at detection with up to 7.5 sec markers prior to that Up to 7.5 sec EGM with first therapy Up to 4.3 sec EGM at termination | X | X |
| Monitored AT/AF | Up to 6 sec EGM ending at detection with up to 7.5 sec markers prior to that | X | X |

Each of the episode types of Table 1 may correspond to certain types of medical devices. An "X" in the "ICD" column indicates that the episode type may be applicable for implantable cardioverter/defibrillator. An "X" in the "IPG" column indicates that the episode type may be applicable for implantable pulse generators. For some of the episode types, the length of time of each portion and/or the endpoints of each portion of the EGM signal data may vary based on when events were detected and/or episode subtypes of the episode type. For example, a treated VT/VF episode type may include up to four different selected portions of the EGM signal data. As another example, a monitored AT/AF episode type may generally include a single selected portion of the EGM signal data.

Table 2 is an example of episode subtypes for the episode type of a treated VT/VF. In other words, the portions for an identified treated VT/VF may be selected in eight different configurations. For example, the episode subtype having zero ATP events and one shock event may have three portions selected from the EGM signal data including a detection portion, a shock portion, and a termination portion. Other episode subtypes may include four portions of the EGM signal data or only two portions of the EGM signal data. As another example, an episode including one ATP sequence and zero shock events may include a portion of the EGM signal data corresponding to the detection of the episode and delivery of the ATP and a portion of the EGM signal data corresponding to termination of the episode.

TABLE 2

| Treated VT/VF Episode Subtype | Portions |
|---|---|
| 0 ATP; 1 shock | Detection: 6 sec (5.9 sec pre-detection + 0.1 sec post-detection) Shock: 9.8 sec (6 sec pre-shock and 3.8 sec post-shock CD), Termination: 2.0 sec (1.9 sec pre-termination + 0.1 post) |
| 2 or more shocks; First and last therapy = shock | Detection: 6 sec (5.9 sec pre-detection + 0.1 sec post-detection) $1^{st}$ Shock: 4.8 sec (1 sec pre and 3.8 sec post shock CD) Last Shock: 4.8 sec (1 sec pre and 3.8 sec post shock CD) Termination: 2 sec (1.9 sec pre-termination + 0.1 post)] |
| 1 or more shock; Last therapy = ATP | Detection: 6 sec (5.9 sec pre-detection + 0.1 sec post-detection) $1^{st}$ Shock: 4.8 sec (1 sec pre and 3.8 sec post shock CD) Last ATP: 4.8 sec (1 sec pre and 3.8 sec post ATP) Termination: 2 sec (1.9 sec pre-termination + 0.1 post)] |

TABLE 2-continued

| Treated VT/VF Episode Subtype | Portions |
|---|---|
| 1 ATP Sequence 0 shocks | Detection and ATP: 15.8 sec ($1^{st}$ row: 5.9 sec pre-detection + 0.1 sec post-detection, $2^{nd}$ row: pre-ATP, ATP, post-ATP) Termination: 2.0 sec (1.9 sec pre-termination + 0.1 post)] |
| 2 or more ATP Sequences; 0 shocks | Detection and Fist ATP: 10.8 sec ($1^{st}$ row: 5.9 sec pre-detection + 0.1 sec post-detection, $2^{nd}$ row: pre-ATP, ATP, post-ATP) Last ATP: 4.8 sec (1 sec pre and 3.8 sec post ATP) Termination: 2 sec (1.9 sec pre-termination + 0.1 post)] |
| Starts with ATP; Last therapy = shock | Detection and First ATP: 10.8 sec ($1^{st}$ row: 5.9 sec pre-detection + 0.1 sec post-detection, $2^{nd}$ row: pre-ATP, ATP, post-ATP) Last shock: 4.8 sec (1 sec pre and 3.8 sec post last shock CD) Termination: 2 sec (1.9 sec pre-termination + 0.1 post)] |
| 1 or more aborted shock; 0 ATP; 0 shock | Detection: 6 sec (5.9 sec pre-detection + 0.1 sec post-detection) Shock: 9.8 sec (6 sec pre and 3.8 sec post $1^{st}$ aborted shock) Termination: 2.0 sec (1.9 sec pre-termination + 0.1 post)] |
| 0 ATP; 0 shocks; 0 aborted shocks | Pre and Post-Detection: 15.8 sec ($1^{st}$ row: 5.9 sec pre-detection + 0.1 sec post-detection, $2^{nd}$ row 9.8 sec) Termination: 2.0 sec (1.9 sec pre-termination + 0.1 post)] |

Table 3 includes example episode subtypes for the treated AT/AF episode subtypes. Although Table 3 only includes two different subtypes of the episode specifying three portions of the EGM signal data each, additional and/or alternative subtypes may be provided in other examples.

TABLE 3

| Treated AT/AF Episode Subtype | Portions |
|---|---|
| First therapy is a delivered ATP or shock | Detection: Up to 6 sec (6 sec pre-detection + 0.1 sec post-detection) First therapy: 7.5 sec (2.5 sec pre and 5 sec post $1^{st}$ therapy ($1^{st}$ ATP pulse or $1^{st}$ shock CD)) Termination: 4.3 sec (4.2 sec pre-termination + 0.1 post)] |
| First therapy is aborted ATP or aborted shock | Detection: Up to 6 sec (6 sec pre-detection + 0.1 sec post-detection) First Therapy: 7.5 sec (2.5 sec pre and 5 sec post $1^{st}$ therapy ($1^{st}$ aborted ATP or shock therapy)) Termination: 4.3 sec (4.2 sec pre-termination + 0.1 post)] |

As shown in Tables 2 and 3, the different episode subtypes may be associated with respective selections of portions of the EGM signal data. These respective selections of portions may be different from each other. In some examples, two or more episode subtypes may be associated with respective selections of portions that are the same. In any case, one or more portions of the EGM signal data may be selected according to the classified episode subtype of the EGM signal data.

Table 4 provides example episode types that do not include two or more episode subtypes. Therefore, a single portion of the EGM signal data may be selected when each of these episode types are identified. The starting time point in the portion may be determined by the identified event (e.g., termination or detection of the episode). The starting point of the selected portion may begin after the actual identified event, such as 100 milliseconds (ms) after the event and run for a six second window. In other examples, the episode types of Table 4 may include additional episode subtypes for which different portions of the EGM signal data would be selected.

TABLE 4

| Episode Type | Portions |
| --- | --- |
| VT/NS & High Rate VT NS | Up to 6 seconds of EGM starting with (Termination + 100 ms – 6 sec) |
| Monitored VT | Up to 6 seconds of EGM starting with (Detection + 100 ms – 6 sec) |
| Fast A & V | Up to 6 seconds of EGM starting with (Detection + 100 ms – 6 sec) |
| V Oversensing | Up to 6 seconds of EGM starting with (1$^{st}$ Ventricular beat that VT/VF detection is withheld + 100 ms – 6 sec) |
| SVT: VT/VF therapy withheld | Up to 6 seconds of EGM starting with (1$^{st}$ Ventricular beat that VT/VF detection is withheld + 100 ms – 6 sec) |
| Monitored AT/AF | Up to 6 seconds of EGM starting with (Detection + 100 ms – 6 sec) |

The times for each portion of EGM signal data described in Tables 1-4 may be based on a specific format of the EGM summary. In other words, the EGM summary may need to fit within a patient report having a predetermined amount of space in which to present the EGM summary. Therefore the durations, or time windows, of each portion may be selected to match the format of the patient report or space in which the EGM summary will be presented. However, the EGM summary may be intended to provide a concise representation of the episode, such as including representative EGM signal data for various events of the episode such as onset, detection, a therapy, and/or termination of the episode. Therefore, the selected portion(s) may be shorter than the entire EGM signal data associated with the episode.

Figure 6:
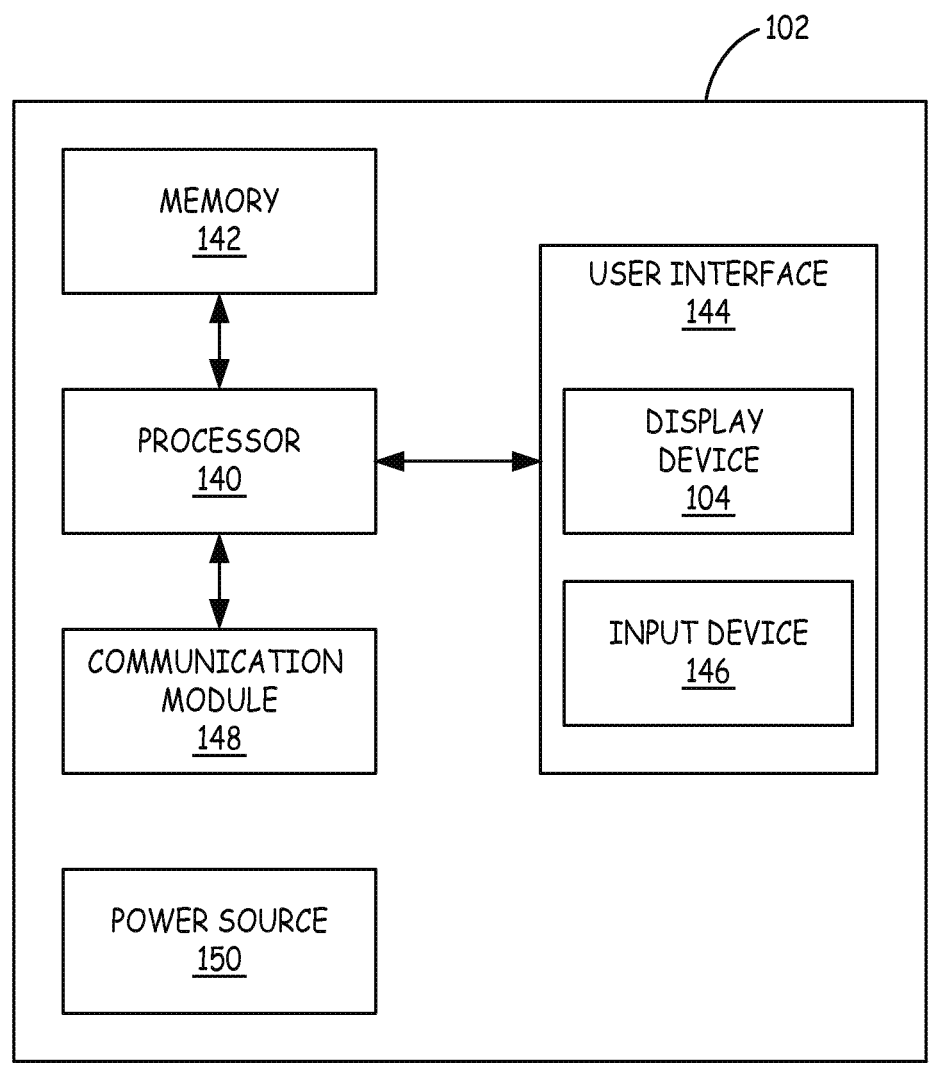
FIG. 6 is a functional block diagram illustrating an example configuration of the computing device of FIG. 1.

FIG. 6 is a functional block diagram illustrating an example configuration of computing device 102 of FIG. 1. Computing device 102 may be a notebook computer, a tablet computer or other mobile device, or workstation, for example. In some examples, computing device 102 may be a medical device programmer such as programmer 24 of FIG. 2. Although computing device 102 may be used by a clinician to display EGM summaries and patient reports received from server 112, computing device 102 may alternatively be configured to perform some or all of the functions attributed to server 122. Computing device 102 may retrieve EGM signal data from memory 142, a medical device that sensed or collected the EGM signal data, and/or repository 114.

As illustrated in FIG. 6, computing device 102 may include a processor 140, a memory 142, a communication module 148, a user interface 144, and a power source 150. Processor 140 stores and retrieves information and instructions to and from memory 142. Processor 140 may include a microprocessor, a microcontroller, a DSP, an ASIC, an FPGA, or other equivalent discrete or integrated logic circuitry. Accordingly, processor 140 may include any suitable structure, whether in hardware, software, firmware or any combination thereof, to perform the functions ascribed herein to processor 140.

Communication module 148 may be configured to receive EGM summaries and patient reports from server 112. Communication module 148 may also receive EGM signal data and other information from IMD 16 and/or other medical devices. If computing device 102 is configured as a medical device programmer, communication module 148 may include hardware to transmit information to and receive information from a medical device. Communication module 148 may also be configured to communicate with server 112 via network 110, for example.

A user, such as a clinician may interact with computing device 102 through user interface 144. User interface 144 may include one or more input devices 146 and one or more display devices 104. In some example, display device 104 and input device 146 may be combined into a presence-sensitive display device (e.g., a touch screen). Display device 104 may be configured to present EGM summaries and patient reports received from server 112. Input device 146 may receive user input and generate indications of the user input for use by user interface 144 and/or processor 140 to navigate within the patient report to other EGM summaries and/or within an EGM summary. In some examples, user interface 144 may also be configured to support an interactive patient report or EGM summary for which the user may request additional data (e.g., the full EGM signal data for the episode of the EGM summary), modify the presentation of data, request a print-out of the EGM summary or patient report, or any other aspect of the patient report of EGM summary. Each EGM summary may include one or more selected portions of EGM signal data to provide retrospective analysis of the EGM signal data to help a user review the patient condition.

Memory 142 may include stored patient reports, EGM summaries, and other information related to one or more patients, the use of computing device 102, software applications, or any other data. If computing device 102 is used to generate EGM summaries, memory 142 may also store EGM summary rules and/or episode classification rules as described with respect to repository 114. Memory 142 may also include instructions for operating user interface 144, communication module 148, and for managing power source 150. Memory 142 may include any volatile or nonvolatile memory such as RAM, ROM, EEPROM or flash memory. Memory 142 may also include a removable memory portion that may be used to provide memory updates or increases in memory capacities. A removable memory may also allow sensitive patient data to be removed before computing device 102 is used by a different patient.

Figure 7:
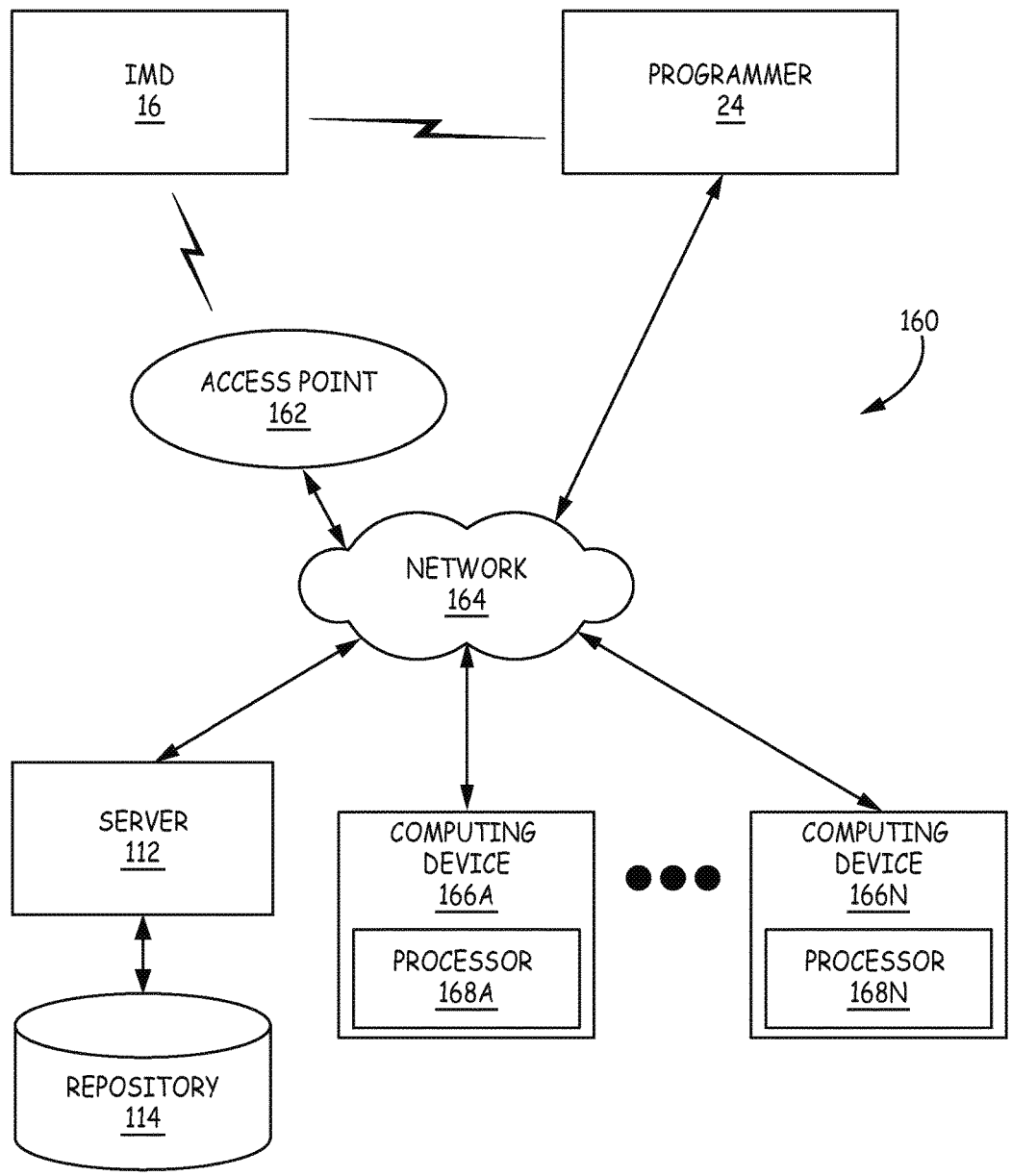
FIG. 7 is a block diagram illustrating an example system that includes the server of FIG. 1 coupled to an IMD and computing devices via a network.

FIG. 7 is a block diagram illustrating an example system that includes the server 112 of FIG. 1 coupled to IMD 16 and computing devices 166 via network 164. System 160 may be similar to system 100 of FIG. 1 or include system 100 in some examples. As shown in FIG. 7, server 112 (e.g., a networked external computing device) and one or more computing devices 166A-166N that are coupled to the IMD 16 and programmer 24 shown in FIG. 2 via a network 164. Network 164 may be generally used to transmit EGM signal data collected by IMD 16 or programmer 24, patient reports and/or EGM summaries, or any other information described herein. In some examples, EGM signal data may be transmitted to an external device for display to a user in the form of EGM summaries with selected portions (i.e., snippets) of the EGM signal data. The EGM signal data may be subjected to retrospective analysis by server 112, programmer 24, and/or at least one of computing device 166 to generate the patient reports and EGM summaries.

In some examples, the information transmitted by IMD 16 may allow a clinician or other healthcare professional to monitor patient 14 remotely. In some examples, IMD 16 may use a telemetry module to communicate with programmer 24 via a first wireless connection, and to communicate with access point 162 via a second wireless connection, e.g., at different times. In the example of FIG. 7, access point 162, programmer 24, server 112 and computing devices 166A-166N are interconnected, and able to communicate with each other through network 164. In some cases, one or more of access point 162, programmer 24, server 112 and computing devices 166A-166N may be coupled to network 164 via one or more wireless connections. IMD 16, programmer 24, server 112, and computing devices 166A-166N may each comprise one or more processors, such as one or more microprocessors, DSPs, ASICs, FPGAs, programmable logic circuitry, or the like, that may perform various functions and operations, such as those described herein.

Access point 162 may comprise a device that connects to network 164 via any of a variety of connections, such as telephone dial-up, digital subscriber line (DSL), or cable modem connections. In other examples, access point 162 may be coupled to network 164 through different forms of connections, including wired or wireless connections. In some examples, access point 162 may be co-located with patient 14 and may comprise one or more programming units and/or computing devices (e.g., one or more monitoring units) that may perform various functions and operations described herein. For example, access point 162 may include a home-monitoring unit that is co-located with patient 14 and that may monitor the activity of IMD 16. In some examples, server 112 or computing devices 166 may control or perform any of the various functions or operations described herein, e.g., select portions of EGM signal data for EGM summaries and transmit the EGM summaries to one or more of computing devices 166 and/or programmer 24.

In some cases, server 112 may be configured to provide a secure storage site for archival of diagnostic information (e.g., occurrence of detection and shock by IMD 16 and attendant circumstances such as the EGM signal leading up to detection) that has been collected and generated from IMD 16 and/or programmer 24. Network 164 may comprise a local area network, wide area network, or global network, such as the Internet. In some cases, programmer 24 or server 112 may assemble EGM signal and diagnosis information in web pages (e.g., as a patient report including one or more EGM summaries) or other documents for viewing by trained professionals, such as clinicians, via viewing terminals associated with computing devices 166. The system of FIG. 7 may be implemented, in some aspects, with general network technology and functionality similar to that provide by the Medtronic CareLink® Network developed by Medtronic, Inc., of Minneapolis, Minn.

Figure 8:
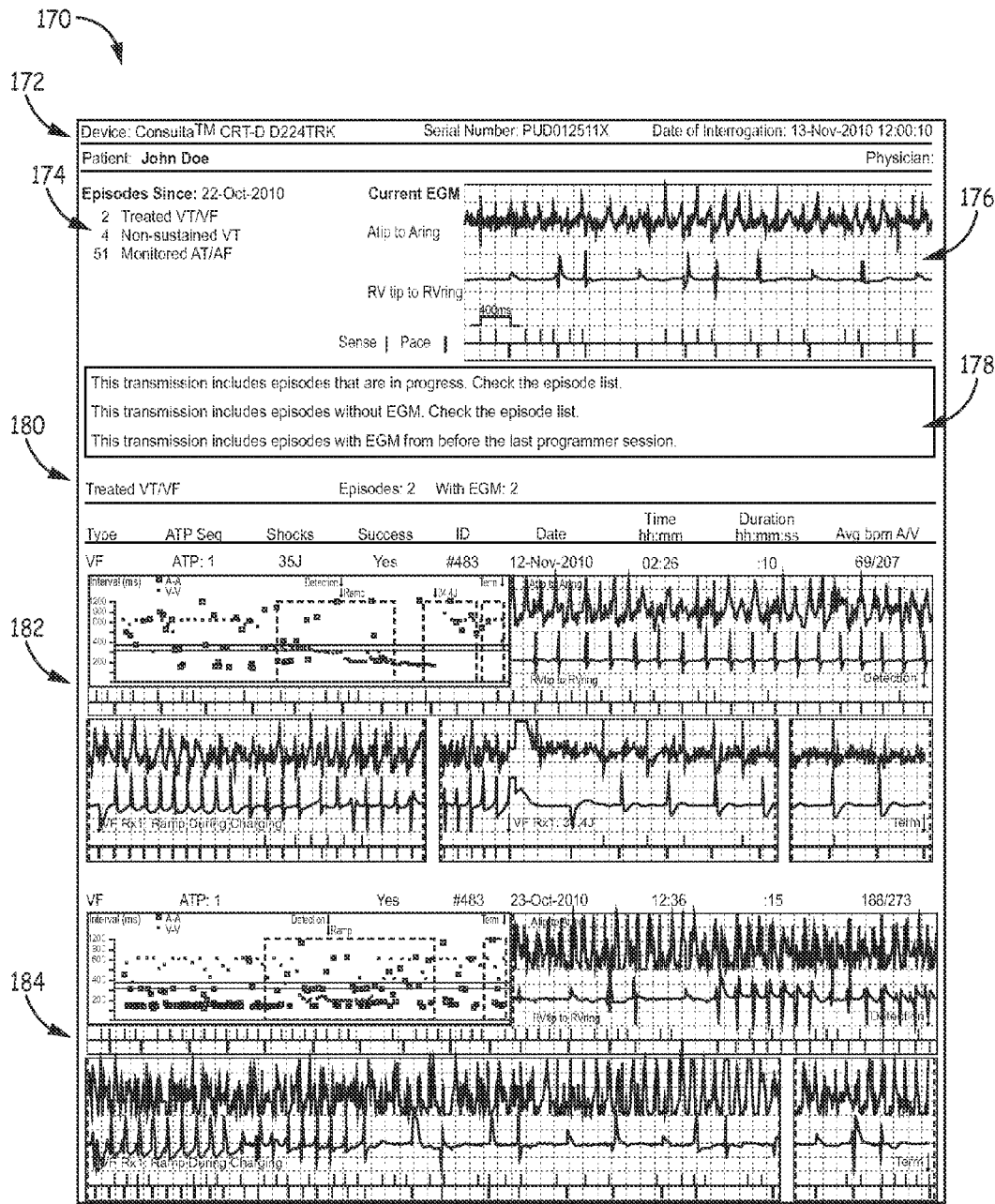
FIG. 8 illustrates an example patient report that includes one or more EGM summaries.

FIG. 8 illustrates example patient report 170 that includes EGM summaries 182 and 184. As shown in FIG. 8, patient report 170 is an example presentation of information related to one or more cardiac episodes of a patient (e.g., patient 12). Patient report 170 may be configured to provide a snapshot of patient data representative of one or more cardiac episodes experienced by the patient. Patient report 170 may include header 172, episode counter 174, current EGM 176, status field 178, episode type indicator 180, and EGM summaries 182 and 184.

Header 172 may include information identifying the patient, a medical device associated with the patient, date of patient report 170, and other identifying information. Episode counter 174 may provide a quantified list of cardiac episodes experienced and detected by the medical device. Current EGM 176 provides a sample of the EGM signal data recently obtained from the patient. Status field 178 includes information about the EGM signal data provided in patient report 170 and/or information about the current status of the patient.

Episode type indicator 180 provides the name of the episode type for which the following EGM summaries are related. EGM summary 182 and EGM summary 184 provides selected portions of the EGM signal data for respective episodes. Each of EGM summaries 182 and 184 may correspond to specific episodes experienced by the patient and include representative portions from which the clinician may be able to evaluate the entire episode. The portions of the EGM signal data for each of EGM summaries 182 and 184 may be selected according to the example Tables herein. Although only two EGM summaries 182 and 184 are shown in FIG. 8, patient report 170 may include any number of EGM summaries that relate to respective episodes experienced by the patient. For example, patient report 170 may include any of EGM summaries 182, 184, 240, 260, 270, and 290 of FIGS. 10-15.

Each of EGM summaries 182 and 184 may be an episode summary for the respective detected cardiac episode (e.g., a treated VT/VF for the example of EGM summaries 182 and 184). EGM summaries 182 and 184 may be organized forms of the episode summary. In other words, an episode summary may include the selected portions of the EGM signal data in an unformatted or formatted configuration. EGM summaries 182 and 184 may be formatted configurations of the respective episode summary. An unformatted or differently formatted episode summary may include the selected portions of EGM signal data as a list of portions and/or without additional information related to the patient and/or the set of EGM signal data such as an interval summary or timeline of markers.

Figure 9:
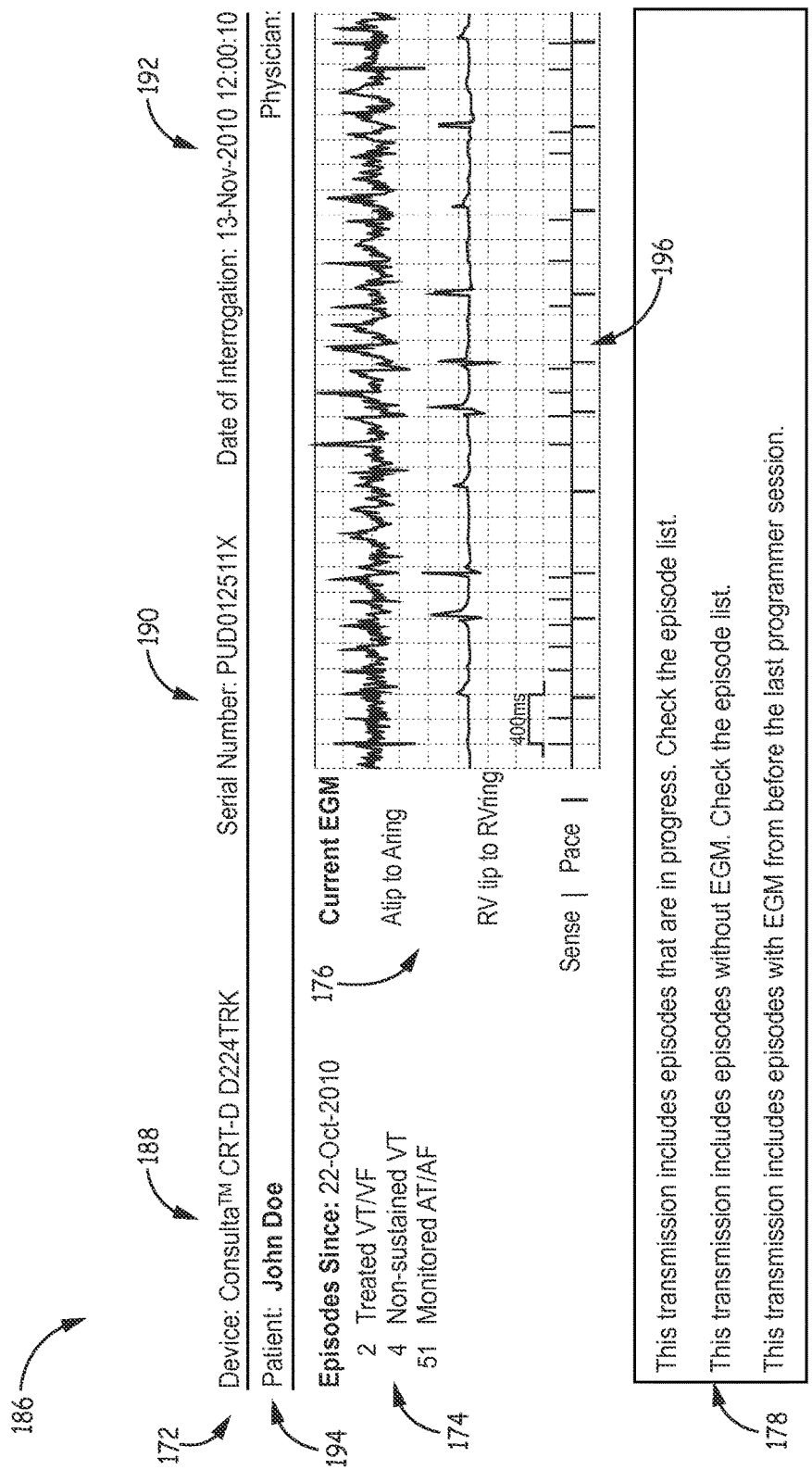
FIG. 9 illustrates an example header section for the patient report of FIG. 8.

FIG. 9 illustrates an example header section 186 for patient report 170 of FIG. 8. As shown in FIG. 9, header section 186 includes header 172, episode counter 174, current EGM 176, and status field 178. Header 172 includes information that may be identifiable of the patient. Header 172 may include device ID 188, device serial number 190, transmission date 192, and patient name 194.

Patient name 194 may identify the name of the patient for which patient report 170 has been generated. Device ID 188 may include the brand and/or model of the medical device from which the EGM signal data has been collected. Device serial number 190 may identify the unique identification number for the medical device. Transmission date 192 may be the date at which the medical device or its programmer was interrogated and data including the EGM signal data was transmitted.

Episode counter 174 may provide indications of which types of episodes have been experienced by the patient and the number of times each of the types of episodes has occurred. Episode counter 174 may also include the beginning date from which the counter started. For example, episode counter 174 of FIG. 9 indicates that 2 treated VT/VF episodes have occurred and 51 monitored AT/AF episodes have occurred.

Current EGM 176 may include current EGM signal data that was retrieved at the most resent time of data transmission (e.g., the date and time of transmission date 192). The EGM signal data may include the signal vector between the atrium tip electrode and the atrium ring electrode and the signal vector between the right ventricle tip electrode and the right ventricle ring electrode. Current EGM 176 may also include marker timeline 196. Marker timeline 196 may include markers for each sensed heart beat and each paced heart beat during the EGM signal data. The sensed beat may be indicated by thin lines and the paced beat may be indicated by thick lines. Status field 178 includes details about the EGM signal data and/or episodes within the data of the transmission, such as whether any episodes in progress, episodes without EGM signal data, and episodes from before the last session are included.

Figure 10:
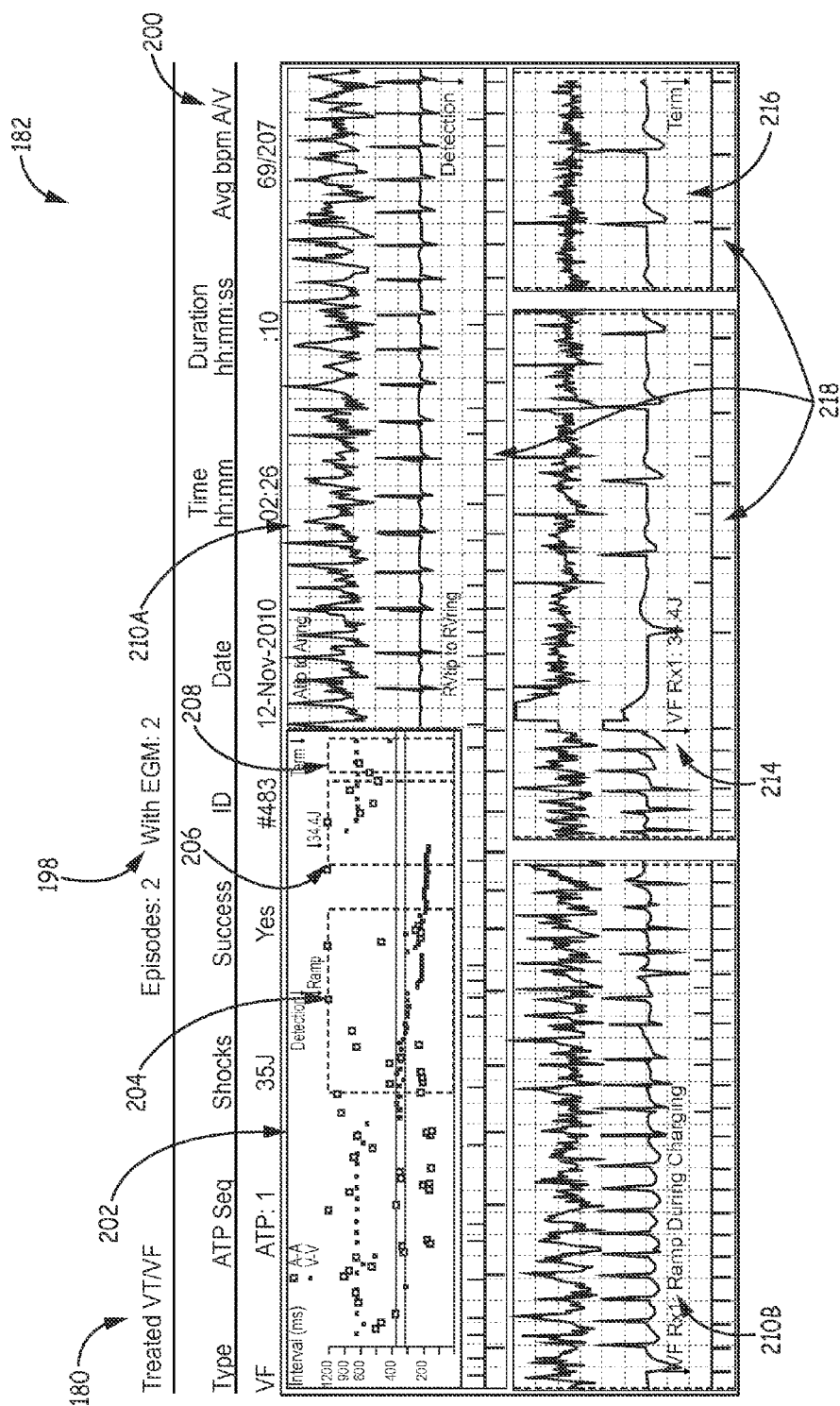
FIG. 10 illustrates an example EGM summary for a treated VT/VF episode type.

FIG. 10 illustrates an example EGM summary 182 for a treated VT/VF episode type. As shown in FIG. 10, EGM summary 182 includes portions of EGM signal data selected based on the episode type of a treated VT/VF. EGM summary 182 includes episode type indicator 180, episode type counter 198, and episode details 200. Episode type indicator 180 indicates the type of episode that was detected within the EGM summary data (e.g., a treated VT/VF). Episode type counter 198 indicates the number of episodes of this episode type have occurred and which episodes include EGM signal data. Episode details 200 provides various information about the episode, treatment, and duration. For example, episode details 200 includes the type of episode, the number of ATP sequences delivered as therapy, the number and/or energy of a delivered shock, the success of any shocks, the date of the episode, the duration of the time and duration of the episode, and/or the average atrial and ventricular contraction rate during the episode.

EGM summary 182 also includes interval plot 202 and portions 210A, 210B, 214, and 216. Interval plot 202 provides a graphical indication of the intervals between consecutive atrial contractions (e.g., open squares) and consecutive ventricular contractions (e.g., closed circles) over at least a portion of the episode. Plot section 204 is a dotted box outlining the detection portion of the episode, plot section 206 is a dotted box outlining the shock therapy portion of the episode, and plot section 208 is a dotted box outlining the termination portion of the episode.

EGM summary 182 includes three different portions corresponding to different events of the episode. Portions 210A and 210B (collectively "portions 210") are related to the detection of the VF episode and charging to provide a therapeutic shock. Portions 210 may be a single selected portion of the EGM signal data, with a break between portions 210A and 210B to wrap the EGM signal data portion to the next line. Portion 214 is related to the delivery of the shock, and portion 216 is related to the termination of the episode. The timing and the duration of each of portions 210A, 210B, 214, and 216 may be determined according to the instructions for the episode type and respective episode subtype of Tables 1, 2, and 5-12.

Each of interval plot 202 and portions 210A, 210B, 212, 214, and 216 are organized above a respective portion of marker timeline 218. Therefore, the EGM signal data of each portion is aligned in time with the respective portion of marker timeline 218. As shown in FIG. 10, the EGM signal data may not include data for the onset of the episode. However, the medical device may collect and store marker information even when EGM signal data is not collected. Therefore, EGM summary 182 may include the portion of marker timeline 218 that corresponds to the onset period for review by the clinician. This portion of marker timeline 218 may be organized under interval plot 202.

Server 112 may not generate EGM summaries with portions having overlapping data. In other words, the time window of each portion may correspond to unique times during the episode. Example Tables 5-14 provide correlations of the timing of events within an episode to specific contents for each portion. In this manner, each portion may be selected according to the identified timing of events such as the detection, therapies, and termination. Each of Tables 5-14 indicate how many portions are to be selected for each set of event conditions (e.g., "timing of events") and the contents of each of the portions. For example, Table 5 provides portions for a treated VT/VF episode type with a subtype of 1 shock.

TABLE 5

Treated VT/VF - 1 shock

| Timing of Events | Portion | Portion Contents |
|---|---|---|
| Duration Detection to Termination ≤12 seconds | First | Up to 18 seconds of EGM starting with (Detection + 100 ms – 6 sec) |
| Duration Detection to Termination >12 seconds; Duration Detection to 1$^{st}$ shock CD >6.1 sec; Duration 1$^{st}$ shock CD to Termination >5.9 seconds | First | Up to 6 seconds of EGM starting with (Detection + 100 ms – 6 sec.) |
|  | Second | 9.8 seconds of EGM starting at (1$^{st}$ shock CD – 6 sec) |
|  | Third | Up to 2 seconds of EGM starting at (Termination + 100 ms – 2 sec) |
| Duration Detection to Termination >12 seconds; Duration Detection to 1$^{st}$ shock CD ≤6.1 sec | First | Up to 15.8 seconds of EGM starting with (Detection + 100 ms – 6 sec) |
|  | Second | Up to 2 seconds of EGM starting with (Termination + 100 ms – 2 sec) |
| Duration Detection to Termination >12 seconds; Duration detection to 1$^{st}$ shock CD >6.1 sec; Duration 1$^{st}$ shock CD to Termination ≤5.9 seconds | First | Up to 6 seconds of EGM starting with (Detection + 100 ms – 6 sec.) |
|  | Second | Up to 12 sec of EGM starting at (1$^{st}$ shock CD – 6 sec) |

Table 6 provides portions for a treated VT/VF episode type with a subtype of two or more shocks.

TABLE 6

Treated VT/VF - 2+ shocks

| Timing of Events | Portion | Portion Contents |
|---|---|---|
| Duration Detection to Termination ≤12 seconds | First | Up to 18 seconds of EGM starting with (Detection + 100 ms – 6 sec) |
| Duration Detection to Termination >12 seconds; Duration detection to 1$^{st}$ shock CD >1.1 sec; Duration 1$^{st}$ shock CD to Last Shock CD >5 sec; Duration Last Shock CD to Termination >5.9 sec | First | Up to 6 seconds of EGM starting with (Detection + 100 ms – 6 sec.) |
|  | Second | 4.8 seconds of EGM starting at (1$^{st}$ shock CD – 1 sec) |
|  | Third | 4.8 seconds of EGM starting at (Last Shock CD – 1 sec) |
|  | Fourth | Up to 2 seconds of EGM starting at (Termination + 100 ms – 2 sec) |
| Duration Detection to Termination >12 seconds; | First | Up to 10.8 seconds of EGM starting with (Detection + 100 ms – 6 sec) |
|  | Second | 4.8 seconds of EGM starting with (Last Shock CD – 1 sec) |

TABLE 6-continued

| Treated VT/VF - 2+ shocks Timing of Events | Portion | Portion Contents |
|---|---|---|
| Duration detection to 1st shock CD ≤1.1 sec; Duration 1st shock CD to Last Shock CD >5 sec; Duration Last Shock CD to Termination >5.9 sec | Third | Up to 2 seconds of EGM starting at (Termination + 100 ms – 2 sec) |
| Duration Detection to Termination >12 seconds; Duration detection to 1st shock CD ≤1.1 sec; Duration 1st shock CD to Last Shock CD >5 sec; Duration Last Shock CD to Termination ≤5.9 sec | First  Second | Up to 10.8 seconds of EGM starting with (Detection + 100 ms – 6 sec)  Up to 7 seconds of EGM starting at (Termination + 100 ms – 7 sec) |
| Duration Detection to Termination >12 seconds; Duration detection to 1st shock CD ≤1.1 sec; Duration 1st shock CD to Last Shock CD ≤5 sec; Duration Last Shock CD to Termination >5.9 sec | First  Second | Up to 15.8 seconds of EGM starting with (Detection + 100 ms – 6 sec)  Up to 2 seconds of EGM starting at (Termination + 100 ms – 2 sec) |
| Duration Detection to Termination >12 seconds; Duration detection to 1st shock CD >1.1 sec; Duration 1st shock CD to Last Shock CD ≤5 sec; Duration Last Shock CD to Termination >5.9 sec | First  Second  Third | Up to 6 seconds of EGM starting with (Detection + 100 ms – 6 sec)  9.8 seconds EGM starting with (1st Shock CD – 1 sec)  Up to 2 seconds of EGM starting at (Termination + 100 ms – 2 sec) |
| Duration Detection to Termination >12 seconds; Duration detection to 1st shock CD >1.1 sec; Duration 1st shock CD to Last Shock CD ≤5 sec; Duration Last Shock CD to Termination ≤5.9 sec | First  Second | Up to 6 seconds of EGM starting with (Detection + 100 ms – 6 sec)  Up to 12 seconds of EGM starting with (1st Shock CD – 1 sec) |
| Duration Detection to Termination >12 seconds; Duration detection to 1st shock CD >1.1 sec; Duration 1st shock CD to Last Shock CD >5 sec; Duration Last Shock CD to Termination ≤5.9 sec | First  Second  Third | Up to 6 seconds of EGM starting with (Detection + 100 ms – 6 sec.)  4.8 seconds of EGM starting at (1st shock CD – 1 sec)  Up to 7 seconds of EGM starting at (Last Shock CD – 1 sec) |

Table 7 provides portions for a treated VT/VF episode type with a subtype of an episode ending in ATP delivery.

TABLE 7

| Treated VT/VF - end in ATP Timing of Events | Portion | Portion Contents |
|---|---|---|
| Duration Detection to Termination ≤12 seconds | First | Up to 18 seconds of EGM starting with (Detection + 100 ms – 6 sec) |
| Duration Detection to Termination >12 seconds; Duration detection to 1st shock CD >1.1 sec; Duration 1st shock CD to Last ATP >5 sec; Duration Last Shock CD to Termination >5.9 sec | First  Second  Third  Fourth | Up to 6 seconds of EGM starting with (Detection + 100 ms – 6 sec.)  4.8 seconds of EGM starting at (1st shock CD – 1 sec)  4.8 seconds of EGM starting at (Last ATP – 1 sec)  Up to 2 seconds of EGM starting at (Termination + 100 ms – 2 sec) |
| Duration Detection to Termination >12 seconds; Duration detection to 1st shock CD ≤1.1 sec; Duration 1st shock CD to Last ATP >5 sec; Duration Last ATP to Termination >5.9 sec | First  Second  Third | Up to 10.8 seconds of EGM starting with (Detection + 100 ms – 6 sec)  4.8 seconds of EGM starting with (Last ATP – 1 sec)  Up to 2 seconds of EGM starting at (Termination + 100 ms – 2 sec) |
| Duration Detection to Termination >12 seconds; Duration detection to 1st shock CD ≤1.1 sec; Duration 1st shock CD to Last ATP >5 sec; Duration Last ATP to Termination ≤5.9 sec | First  Second | Up to 10.8 seconds of EGM starting with (Detection + 100 ms – 6 sec)  Up to 7 seconds of EGM starting with (Last ATP – 1 sec) |
| Duration Detection to Termination >12 seconds; Duration detection to 1st shock CD ≤1.1 sec; Duration 1st shock CD to Last ATP ≤5 sec; Duration Last ATP to Termination >5.9 sec | First  Second | Up to 15.8 seconds of EGM starting with (Detection + 100 ms – 6 sec)  Up to 2 seconds of EGM starting at (Termination + 100 ms – 2 sec) |
| Duration Detection to Termination >12 seconds; Duration detection to 1st shock CD >1.1 sec; Duration 1st shock CD to Last ATP ≤5 sec; Duration Last Shock CD to Termination >5.9 sec | First  Second  Third | Up to 6 seconds of EGM starting with (Detection + 100 ms – 6 sec)  9.8 seconds EGM starting with (1st Shock CD – 1 sec)  Up to 2 seconds of EGM starting at (Termination + 100 ms – 2 sec) |

TABLE 7-continued

| Treated VT/VF - end in ATP Timing of Events | Portion | Portion Contents |
|---|---|---|
| Duration Detection to Termination >12 seconds; Duration detection to 1st shock CD >1.1 sec; Duration 1st shock CD to Last ATP ≤5 sec; Duration Last ATP to Termination ≤5.9 sec | First<br>Second | Up to 6 seconds of EGM starting with (Detection + 100 ms – 6 sec)<br>Up to 12 seconds of EGM starting with (1st Shock CD – 1 sec) |
| Duration Detection to Termination >12 seconds; Duration detection to 1st shock CD >1.1 sec; Duration 1st shock CD to Last ATP >5 sec; Duration Last ATP to Termination ≤5.9 sec | First<br>Second<br>Third | Up to 6 seconds of EGM starting with (Detection + 100 ms – 6 sec.)<br>4.8 seconds of EGM starting at (1st shock CD – 1 sec)<br>Up to 7 seconds of EGM starting at (Last ATP – 1 sec) |

Table 8 provides portions for a treated VT/VF episode type with a subtype of one ATP delivered.

TABLE 8

| Treated VT/VF - 1 ATP Timing of Events | Portion | Portion Contents |
|---|---|---|
| Duration Detection to Termination ≤12 seconds | First | Up to 18 seconds of EGM starting with (Detection + 100 ms – 6 sec) |
| Duration Detection to Termination >12 seconds | First<br>Second | Up to 15.8 seconds of EGM starting with (Detection + 100 ms – 6 sec)<br>Up to 2 seconds of EGM starting with (Termination + 100 ms – 2 sec) |

Table 9 provides portions for a treated VT/VF episode type with a subtype of two or more ATP deliveries and zero shocks.

TABLE 9

| Treated VT/VF - 2+ ATP & 0 shocks Timing of Events | Portion | Portion Contents |
|---|---|---|
| Duration Detection to Termination ≤12 seconds | First | Up to 18 seconds of EGM starting with (Detection + 100 ms – 6 sec) |
| Duration Detection to Termination >12 seconds; Duration Detection to last ATP >6.1 sec; Duration | First<br>Second<br>Third | Up to 10.8 seconds of EGM starting with (Detection + 100 ms – 6 sec.)<br>4.8 seconds of EGM starting at (Last ATP – 1 sec)<br>Up to 2 seconds of EGM starting at (Termination + 100 ms – 2 sec) |

TABLE 9-continued

| Treated VT/VF - 2+ ATP & 0 shocks Timing of Events | Portion | Portion Contents |
|---|---|---|
| last ATP to Termination >5.9 seconds Duration Detection to Termination >12 seconds; Duration Detection to last ATP ≤6.1 sec; Duration last ATP to Termination >5.9 seconds | First<br>Second | Up to 15.8 seconds of EGM starting with (Detection + 100 ms – 6 sec)<br>Up to 2 seconds of EGM starting with (Termination + 100 ms – 2 sec) |
| Duration Detection to Termination >12 seconds | First<br>Second | Up to 15.8 seconds of EGM starting with (Detection + 100 ms – 6 sec)<br>Up to 2 seconds of EGM starting with (Termination + 100 ms – 2 sec) |

Table 10 provides portions for a treated VT/VF episode type with a subtype of one or more ATP deliveries and one or more shocks.

TABLE 10

| Treated VT/VF - 1+ ATP & 1+ shock Timing of Events | Portion | Portion Contents |
|---|---|---|
| Duration Detection to Termination ≤12 seconds | First | Up to 18 seconds of EGM starting with (Detection + 100 ms – 6 sec) |
| Duration Detection to Termination >12 seconds; Duration Detection to last ATP >6.1 sec; Duration last ATP to Termination >5.9 seconds | First<br>Second<br>Third | Up to 10.8 seconds of EGM starting with (Detection + 100 ms – 6 sec.)<br>4.8 seconds of EGM starting at (Last Shock CD – 1 sec)<br>Up to 2 seconds of EGM starting at (Termination + 100 ms – 2 sec) |
| Duration Detection to Termination >12 seconds; Duration Detection to last ATP ≤6.1 sec; Duration last ATP to Termination >5.9 seconds | First<br>Second | Up to 15.8 seconds of EGM starting with (Detection + 100 ms – 6 sec)<br>Up to 2 seconds of EGM starting with (Termination + 100 ms – 2 sec) |
| Duration Detection to Termination >12 seconds; Duration Detection to last shock CD >6.1 sec Duration last shock CD to Termination ≤5.9 seconds | First<br>Second | Up to 10.8 seconds of EGM starting with (Detection + 100 ms – 6 sec.)<br>Up to 7 seconds of EGM starting at (last shock CD – 1 sec) |

Table 11 provides portions for a treated VT/VF episode type with a subtype of an episode with only aborted shocks (e.g., no shocks were delivered even though charging occurred).

TABLE 11

| Treated VT/VF - only aborted shocks Timing of Events | Portion | Portion Contents |
|---|---|---|
| Duration Detection to Termination ≤12 seconds | First | Up to 18 seconds of EGM starting with (Detection + 100 ms - 6 sec) |
| Duration Detection to Termination >12 seconds; Duration Detection to first aborted shock >6.1 sec; Duration first aborted shock CD to Termination >5.9 seconds | First | Up to 6 seconds of EGM starting with (Detection + 100 ms - 6 sec.) |
| | Second | 9.8 seconds of EGM starting at (1$^{st}$ aborted shock CD - 6 sec) |
| | Third | Up to 2 seconds of EGM starting at (Termination + 100 ms - 2 sec) |
| Duration Detection to Termination >12 seconds; Duration Detection to first aborted shock CD ≤6.1 sec | First | Up to 15.8 seconds of EGM starting with (Detection + 100 ms - 6 sec) |
| | Second | Up to 2 seconds of EGM starting with (Termination + 100 ms - 2 sec) |
| Duration Detection to Termination >12 seconds; Duration Detection to first aborted shock CD >6.1 sec Duration first aborted shock CD to Termination ≤5.9 seconds | First | Up to 6 seconds of EGM starting with (Detection + 100 ms - 6 sec.) |
| | Second | Up to 12 seconds of EGM starting at (1$^{st}$ aborted shock CD - 6 sec) |

Table 12 provides portions for a treated VT/VF episode type with a subtype of zero shocks and zero ATP deliveries.

TABLE 12

| Treated VT/VF - 0 shocks & 0 ATP Timing of Events | Portion | Portion Contents |
|---|---|---|
| Duration Detection to Termination ≤12 seconds | First | Up to 18 seconds of EGM starting with (Detection + 100 ms - 6 sec) |
| Duration Detection to Termination >12 seconds | First | Up to 15.8 seconds of EGM starting with (Detection + 100 ms - 6 sec) |
| | Second | Up to 2 seconds of EGM starting with (Termination + 100 ms - 2 sec) |

Table 13 provides portions for a treated AT/AF episode type with a subtype of one or more therapies delivered.

TABLE 13

| Treated AT/AF - 1+ therapies Timing of Events | Portion | Portion Contents |
|---|---|---|
| Duration Detection to Termination ≤12 seconds | First | Up to 18 seconds of EGM starting with (Detection + 100 ms - 6 sec) |

TABLE 13-continued

| Treated AT/AF - 1+ therapies Timing of Events | Portion | Portion Contents |
|---|---|---|
| Duration Detection to Termination >12 seconds; Duration Detection to 1$^{st}$ therapy >2.6 sec; Duration 1$^{st}$ therapy to Termination >9.4 seconds | First | Up to 6 seconds of EGM starting with (Detection + 100 ms - 6 sec.) |
| | Second | 7.5 seconds of EGM starting at (1$^{st}$ Rx - 2.5 sec) |
| | Third | Up to 4.3 seconds of EGM starting at (Termination + 100 ms - 4.3 sec) |
| Duration Detection to Termination >12 seconds; Duration Detection to 1$^{st}$ therapy ≤2.6 sec; Duration 1$^{st}$ therapy to Termination >9.4 seconds | First | Up to 13.5 seconds of EGM starting with (Detection + 100 ms - 6 sec) |
| | Second | Up to 4.3 seconds of EGM starting with (Termination + 100 ms - 4.3 sec) |
| Duration Detection to Termination >12 seconds; Duration Detection to 1$^{st}$ therapy >2.6 sec; Duration 1$^{st}$ therapy to Termination ≤9.4 seconds | First | Up to 6 seconds of EGM starting with (Detection + 100 ms - 6 sec.) |
| | Second | Up to 12 sec of EGM starting at (1$^{st}$ therapy - 2.5 sec) |

Table 14 provides portions for a treated AT/AF episode type with a subtype of aborted therapies (e.g., no therapies were delivered even though charging occurred).

TABLE 14

| Treated AT/AF - aborted therapies Timing of Events | Portion | Portion Contents |
|---|---|---|
| Duration Detection to Termination ≤12 seconds | First | Up to 18 seconds of EGM starting with (Detection + 100 ms - 6 sec) |
| Duration Detection to Termination >12 seconds; Duration Detection to 1$^{st}$ aborted therapy >2.6 sec; Duration 1$^{st}$ aborted therapy to Termination >9.4 seconds | First | Up to 6 seconds of EGM starting with (Detection + 100 ms - 6 sec.) |
| | Second | 7.5 seconds of EGM starting at (1$^{st}$ aborted therapy - 2.5 sec) |
| | Third | Up to 4.3 seconds of EGM starting at (Termination + 100 ms - 4.3 sec) |
| Duration Detection to Termination >12 seconds; Duration Detection to 1$^{st}$ aborted therapy ≤2.6 sec; Duration 1$^{st}$ | First | Up to 13.5 seconds of EGM starting with (Detection + 100 ms - 6 sec) |
| | Second | Up to 4.3 seconds of EGM starting with (Termination + 100 ms - 4.3 sec) |

TABLE 14-continued

Treated
AT/AF - aborted
therapies
Timing of
Events | Portion | Portion Contents
---|---|---
aborted therapy to Termination >9.4 seconds Duration Detection to Termination >12 seconds; Duration Detection to 1$^{st}$ aborted therapy >2.6 sec; Duration 1$^{st}$ aborted therapy to Termination ≤9.4 seconds | First | Up to 6 seconds of EGM starting with (Detection + 100 ms − 6 sec.)
 | Second | Up to 12 sec of EGM starting at (1$^{st}$ aborted therapy − 2.5 sec)

Each of Tables 5-14 are provided as merely one example of a number of portions and portion contents for several episode types and episode subtypes. Tables 5-14, e.g., the techniques or decision logic illustrated by Tables 5-14, may also be used to select the portions for the EGM summaries of FIGS. 11-16 herein. In other examples, different events, timings, and contents may be specified based on the desired format of the EGM summary, clinician preferences, or any other criteria.

Figure 11:
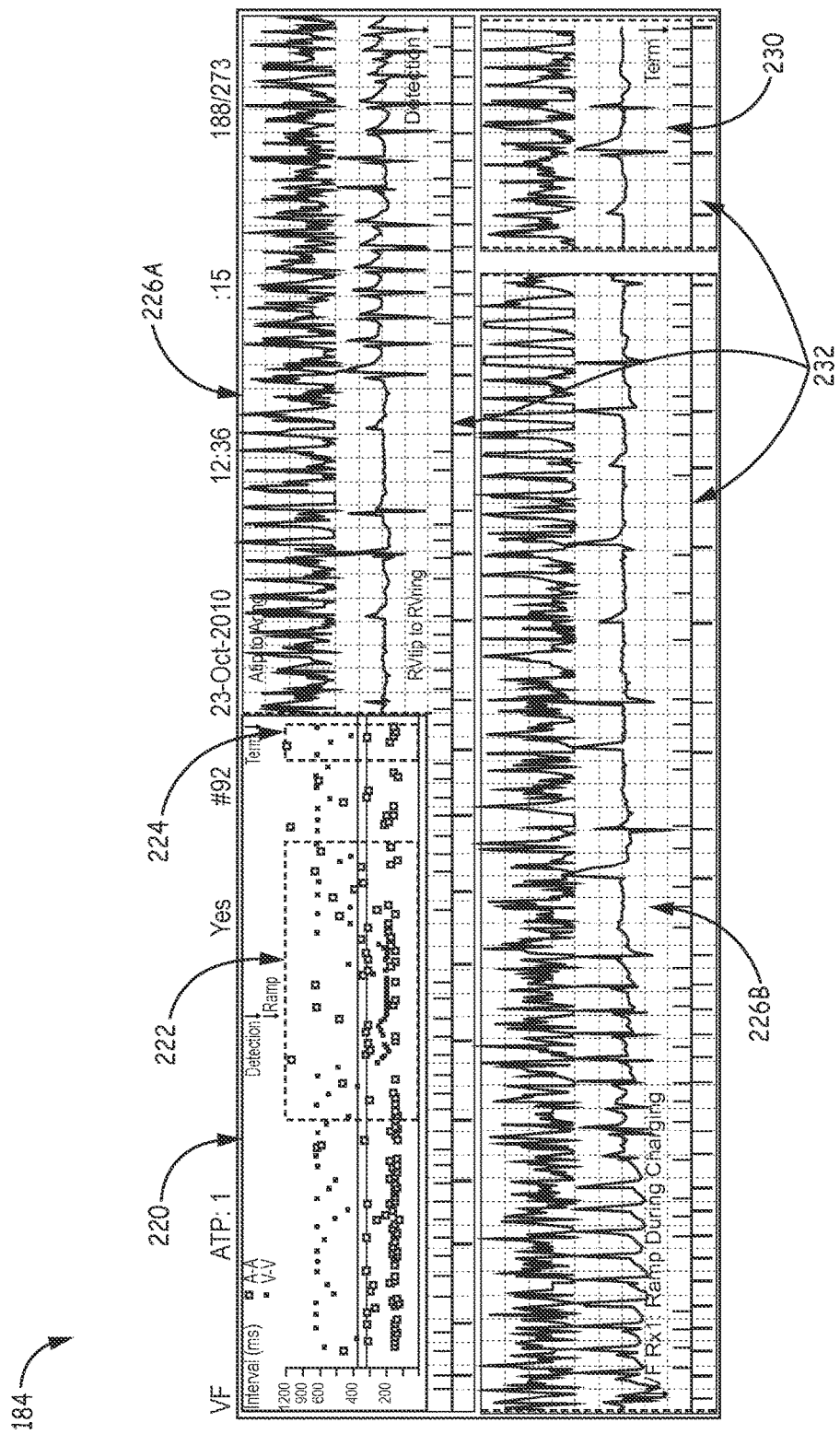
FIG. 11 illustrates another example EGM summary for a treated VT/VF episode type.

FIG. 11 illustrates another example EGM summary 184 for a treated VT/VF episode type. EGM summary 184 may be similar to EGM summary 182 of FIG. 10. As shown in FIG. 11, EGM summary 184 includes portions of EGM signal data selected based on the episode type of a treated VT/VF. Although, a shock was aborted ATP therapy was delivered during charging of the medical device in preparation for the subsequently aborted shock. EGM summary 184 includes interval plot 220 and portions 226A, 226B, and 230. Interval plot 220 provides a graphical indication of the intervals between consecutive atrial contractions (e.g., open squares) and consecutive ventricular contractions (e.g., closed circles) over at least a portion of the episode. Plot section 222 is a dotted box outlining the detection portion of the episode and plot section 224 is a dotted box outlining the termination portion of the episode.

EGM summary 184 includes two different portions corresponding to different events of the episode. Portions 226A and 226B (collectively "portions 226") are related to the detection of the VF episode and charging to provide a therapeutic shock. Portions 226 may be a single selected portion of the EGM signal data, with a break between portions 226A and 226B to wrap the EGM signal data portion to the next line. Portion 230 is related to the termination of the episode. The timing and the duration of each of portions 226A and 226B, and 230 may be determined according to the instructions for the episode type and respective episode subtype of Tables 1, 2, and 5-12. Each of interval plot 220 and portions 226A and 226B, and 230 are organized above a respective portion of marker timeline 230. Marker timeline 230 may be generated from marker channel data stored by the medical device.

Figure 12:
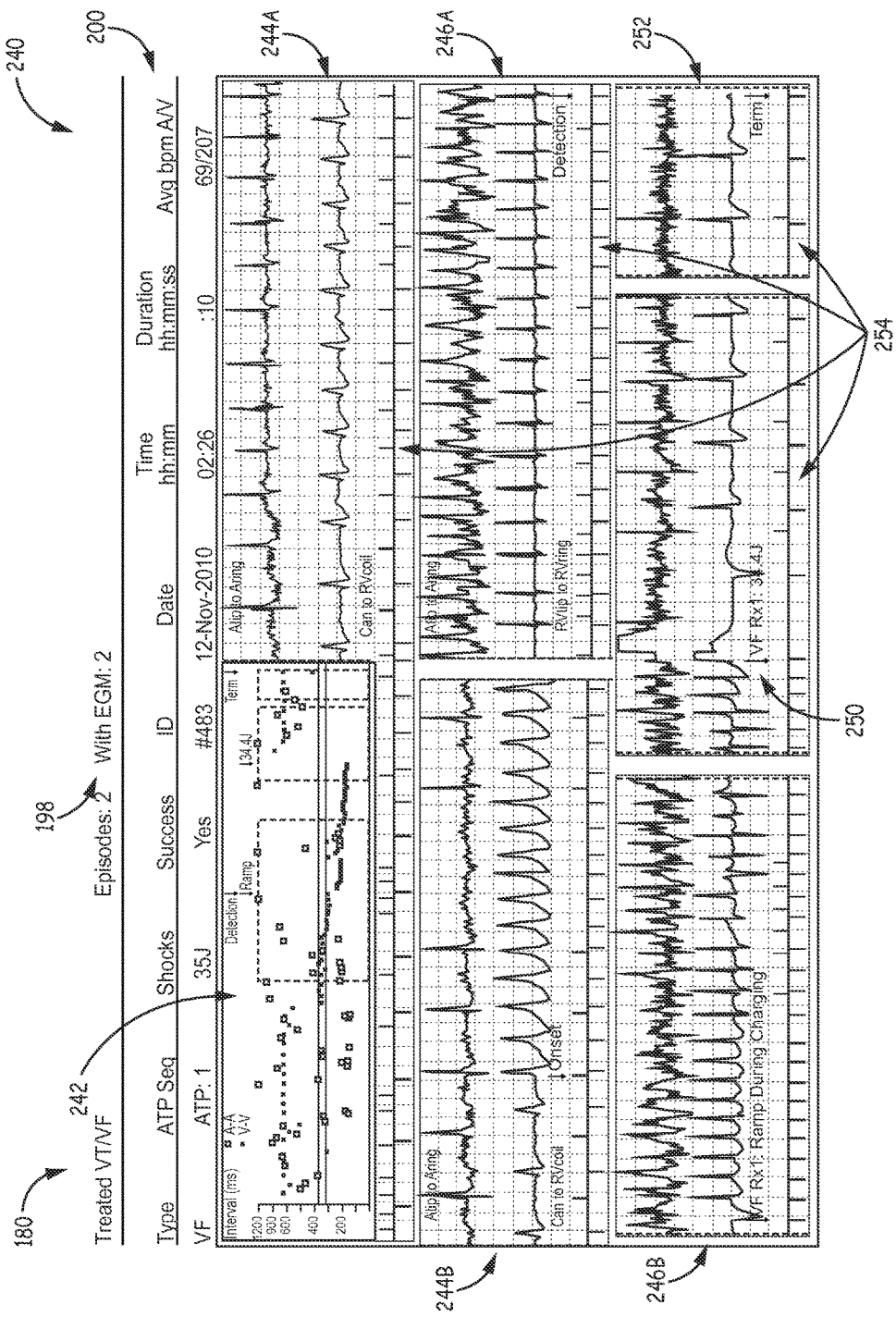
FIG. 12 illustrates another example EGM summary with an onset portion of EGM signal data for a treated VT/VF episode type.

FIG. 12 illustrates another example EGM summary 240 with an onset portion 244 of EGM signal data for a treated VT/VF episode type. EGM summary 240 may be substantially similar to EGM summary 182 of FIG. 10. However, EGM summary 240 may include the onset portion of EGM signal data. As shown in FIG. 12, EGM summary 240 includes portions of EGM signal data selected based on the episode type of a treated VT/VF. EGM summary 240 includes episode type indicator 180, episode type counter 198, and episode details 200.

EGM summary 240 also includes interval plot 242 and portions 244A, 244B (collectively "portions 244"), portions 246A and 246B (collectively "portions 246"), portion 250, and portion 252. Interval plot 242 provides a graphical indication of the intervals between consecutive atrial contractions (e.g., open squares) and consecutive ventricular contractions (e.g., closed circles) over at least a portion of the episode. In addition, EGM summary 240 includes portions 244 which correspond to EGM signal data collected during the onset of the detected episode. The onset portion may include EGM signal data prior to when the medical device detected the episode. Portions 244 may be organized between interval plot 242 and portions 246 corresponding to the detection of the episode.

EGM summary 240 also includes three additional portions. Portions 246A and 246B (collectively "portions 246") related to the detection of the VF episode and charging to provide a therapeutic shock, portion 250 is related to the delivery of the shock, and portion 252 is related to the termination of the episode. Each of interval plot 242 and portions 244, 246, 250, and 252 are organized above a respective portion of marker timeline 254. Therefore, the EGM signal data of each portion is aligned in time with the respective portion of marker timeline 254.

Figure 13:
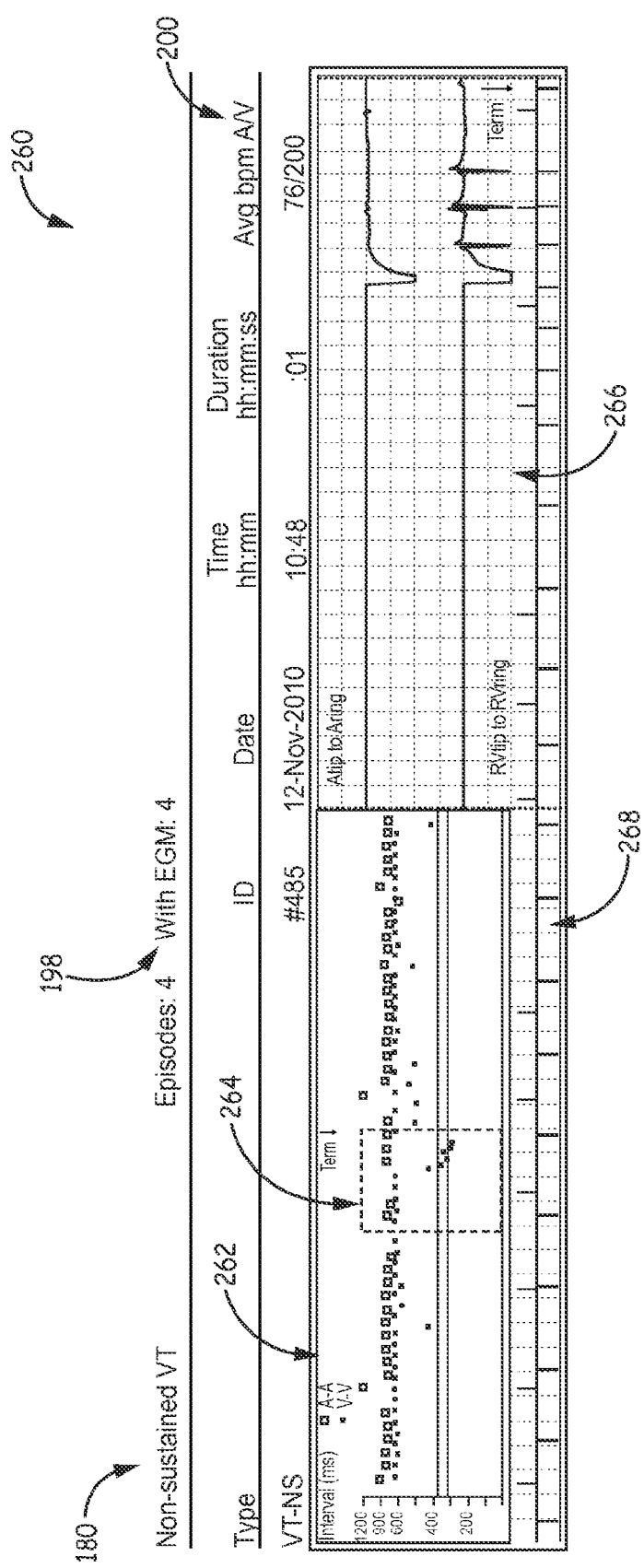
FIG. 13 illustrates an example EGM summary for a non-sustained VT episode type.

FIG. 13 illustrates an example EGM summary 260 for a non-sustained VT episode type. As shown in FIG. 13, EGM summary 260 includes portions of EGM signal data selected based on the episode type of a non-sustained VT. EGM summary 260 includes episode type indicator 180, episode type counter 198, and episode details 200 similar to EGM summary 182. Episode type indicator 180 indicates the type of episode that was detected within the EGM summary data (e.g., a non-sustained VT). Episode type counter 198 indicates the number of episodes of this episode type have occurred and which episodes include EGM signal data. Episode details 200 provides various information about the episode, treatment, and duration. For example, episode details 200 includes the type of episode, the date of the episode, the duration of the time and duration of the episode, and/or the average atrial and ventricular contraction rate during the episode.

EGM summary 260 also includes interval plot 262 and portion 266. Interval plot 262 provides a graphical indication of the intervals between consecutive atrial contractions (e.g., open squares) and consecutive ventricular contractions (e.g., closed circles) over at least a portion of the episode. Plot section 264 is a dotted box outlining the termination portion that corresponds to portion 266. Portion 266 is the portion selected to represent the non-sustained VT of the episode, which illustrates that the VT eventually terminated. Portion 266 of the EGM signal data and interval plot 262 is organized above the corresponding markers of marker timeline 268.

Figure 14:
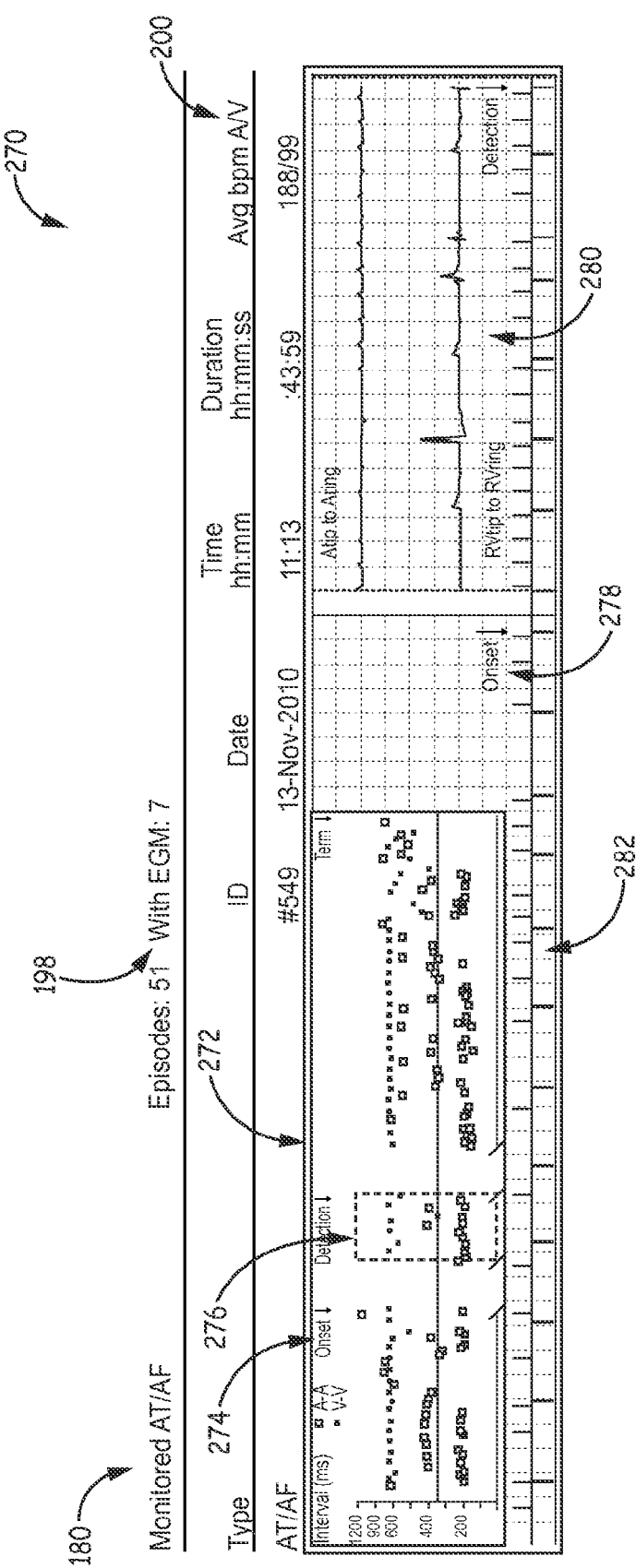
FIG. 14 illustrates an example EGM summary for a monitored AT/AF episode type.

FIG. 14 illustrates an example EGM summary 270 for a monitored AT/AF episode type. As shown in FIG. 14, EGM summary 270 includes portions of EGM signal data selected based on the episode type of a monitored AT/AF. EGM summary 270 includes episode type indicator 180, episode type counter 198, and episode details 200 similar to EGM summary 182. Episode type indicator 180 indicates the type of episode that was detected within the EGM summary data (e.g., a monitored AT/AF). Episode type counter 198 indicates the number of episodes of this episode type have occurred and which episodes include EGM signal data. Episode details 200 provides various information about the episode, treatment, and duration. For example, episode details 200 includes the type of episode, the date of the episode, the duration of the time and duration of the episode, and/or the average atrial and ventricular contraction rate during the episode.

EGM summary 270 also includes interval plot 272 and portions 278 and 280. Interval plot 262 provides a graphical indication of the intervals between consecutive atrial contractions (e.g., open squares) and consecutive ventricular contractions (e.g., closed circles) over at least a portion of the episode. Plot section 274 indicates where the onset of the AT/AF episode occurred. Plot section 276 is a dotted box outlining the detection portion that corresponds to portion 280. Portion 278 indicates where onset EGM signal data would occur if it were stored by the medical device. Portion 280 is the portion selected to represent the detection of the AT/AF episode. Portion 280 of the EGM signal data and interval plot 272 are organized above the corresponding markers of marker timeline 282.

Figure 15:
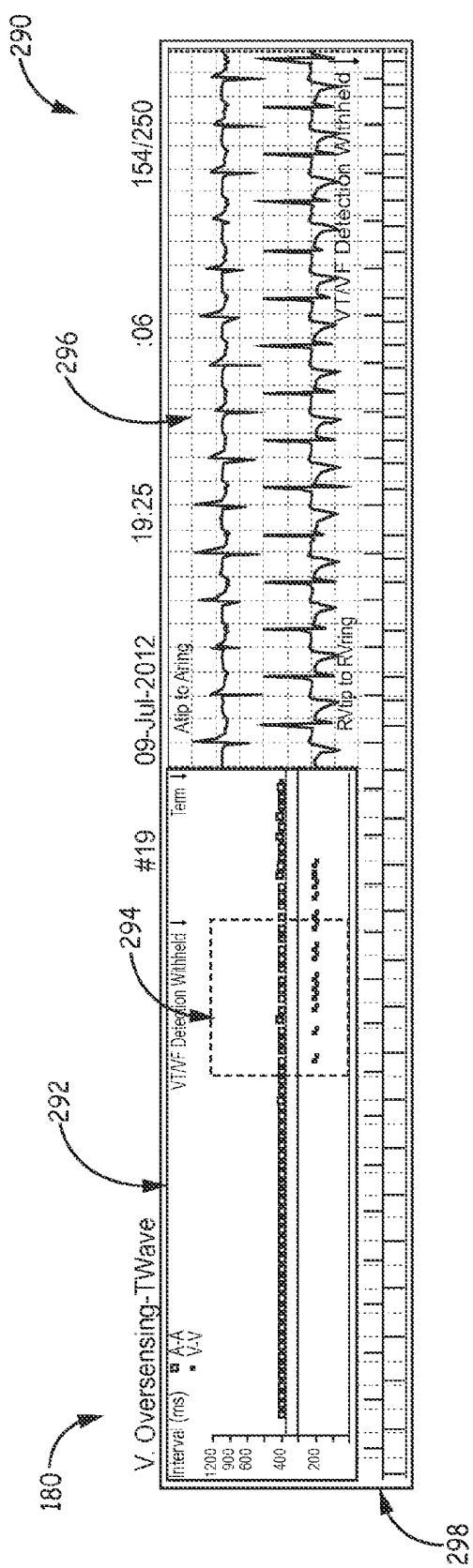
FIG. 15 illustrates an example EGM summary for an oversensing T-wave episode type.

FIG. 15 illustrates an example EGM summary 290 for an oversensing T-wave episode type. As shown in FIG. 15, EGM summary 290 includes portions of EGM signal data selected based on the episode type of an oversensing T-wave. EGM summary 290 includes episode type indicator 180, and may include any other details related to the EGM summary. EGM summary 290 also includes interval plot 292 and portion 296. Interval plot 292 provides a graphical indication of the intervals between consecutive atrial contractions (e.g., open squares) and consecutive ventricular contractions (e.g., closed circles) over at least a portion of the episode. Plot section 294 is a dotted box outlining the portion in which the detection of VT/VF was withheld that corresponds to portion 296. Portion 296 indicates the portion of the EGM signal data that includes signals from which the medical device determined to withhold detection of a VT/VF episode.

Figure 16:
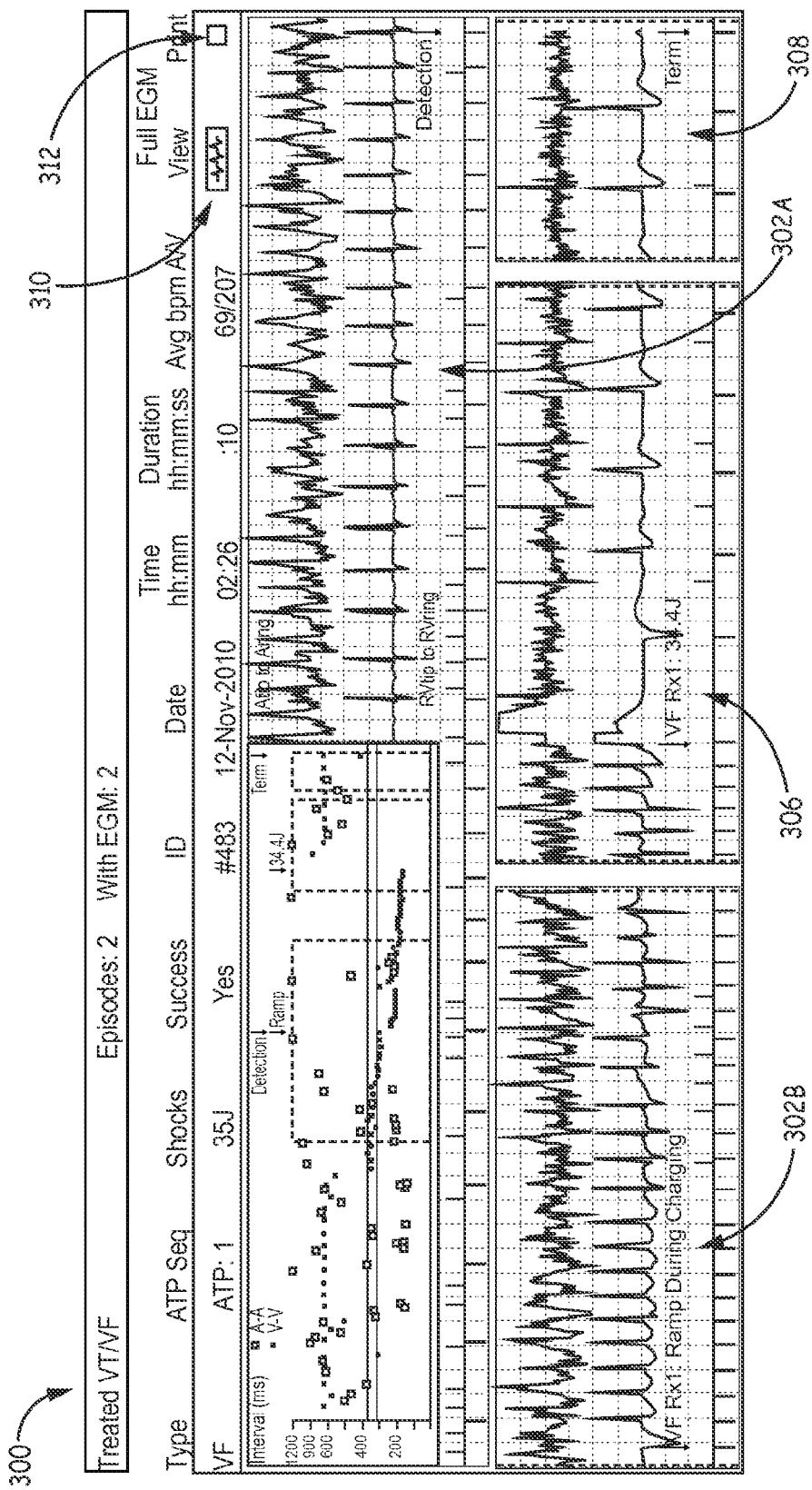
FIG. 16 illustrates an example interactive EGM summary for a treated VT/VF episode type.

FIG. 16 illustrates an example interactive EGM summary 300 for a treated VT/VF episode type. EGM summary 300 may include similar data as shown in EGM summary 182 of FIG. 10. However, EGM summary 300 may be interactive such that the user may submit a request to retrieve additional information regarding some or all of the shown in formation. As shown in FIG. 16, EGM summary 300 includes portions of EGM signal data selected based on the episode type of a treated VT/VF. EGM summary 300 includes portions 302A and 302B (collectively "portions 302"), portion 306, and portion 308 as the selected portions of the EGM signal data.

In addition to EGM summary 182, EGM summary 300 includes interactive features and, more particularly, full EGM button 310 and print button 312. Full EGM button 310 may be an input that, when selected, prompts server 112 to retrieve the full EGM signal data for the episode represented by EGM summary 300 from repository 114 and output the full EGM signal data for presentation to the user. The full EGM signal data may include all the signal information starting at onset or detection of the episode and ending after termination of the episode. In another example, the computing device (e.g., computing device 102) may generate a printout of EGM summary 300 or the full EGM signal data in response to receiving an indication of the selection of print button 312.

EGM summary 300 may provide additional interactive functionality in other examples. For example, in response to receiving an indication selecting one of portions 302, 306, and 308, computing device 102 may enlarge an area of portion corresponding to the selection. EGM summary 300 may also support scrolling of EGM signal data within each portion or other navigation within the EGM signal data. The patient report (e.g., patient report 170) may also be interactive. In this manner, the computing device may support navigation to different EGM summaries, within EGM portions, or other aspects of the EGM signal data.

Figure 17A:
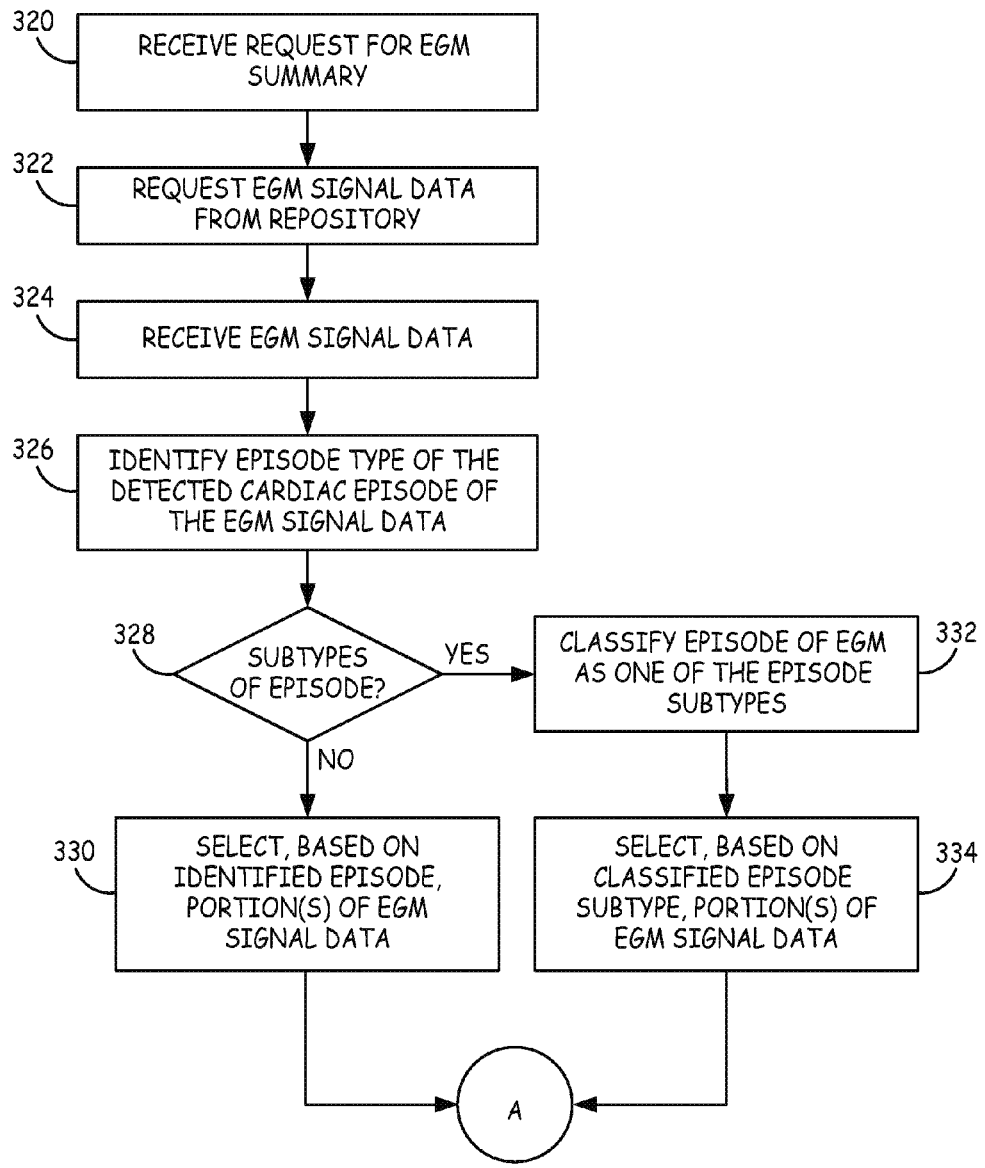
FIGS. 17A and 17B are flow diagrams of an example process for outputting an EGM summary with portions of EGM signal data selected based on an episode type of a detected cardiac episode, in accordance with one or more aspects of the disclosure.
Figure 17B:
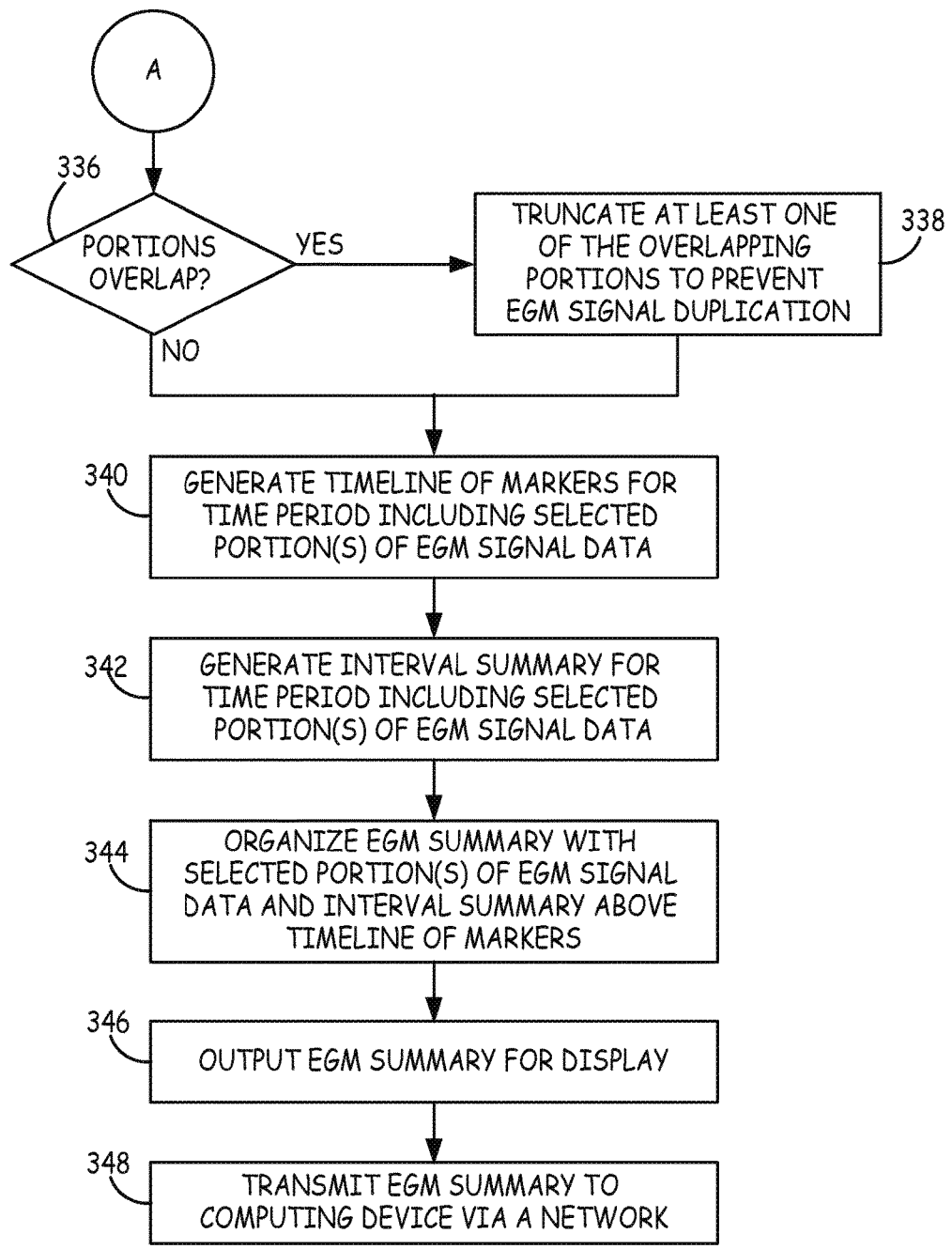

FIGS. 17A and 17B are flow diagrams of an example process for outputting an EGM summary with portions of EGM signal data selected based on an episode type of a detected cardiac episode, in accordance with one or more aspects of the disclosure. The process of FIGS. 17A and 17B will be described with respect to EGM summary module 130 of server 112, as one example. However, the process of FIGS. 17A and 17B may alternatively be performed by processor 140 of computing device 102, one or more processors of programmer 24, or any other computing device. In addition, one or more aspects of FIGS. 17A and 17B may be distributed across two or more devices via network 110 or 164.

As shown in FIG. 17A, EGM summary module 130 is configured to receive an indication of a request for an EGM summary (e.g., EGM summary 182) or patient report that includes one or more EGM summaries (320). Alternatively, processors 122 or EGM summary module 130 may determine that an EGM summary is to be generated and transmitted for presentation based on a predetermined schedule (e.g., time of day or day of week). In response to receiving the indication of the request, EGM summary module 130 may request EGM signal data from repository 114 that corresponds to one or more episodes (322). EGM summary module 130 may then receive the EGM signal data from repository 114 (324).

EGM summary module 130 may next identify the episode type of the detected cardiac episode of the received EGM summary data (326). EGM summary module 130 may look for an identifier within the EGM signal data placed by the medical device when the data was collected. Alternatively, EGM summary module 130 may analyze the EGM signal data and identify the episode type based on one or more characteristics of the episode type within the EGM signal data. If the identified episode type is not related to any episode subtypes ("NO" branch of block 328), EGM summary module 130 may select, based on the identified episode, one or more portions of the EGM signal data to include in the EGM summary.

As described herein, EGM summary module 130 may determine the episode type by identifying the EGM signal data as including an episode of one of the plurality of possible episode types. In some examples, the EGM signal data may be annotated or otherwise include an indication of the episode type, where the medical device that detected the cardiac episode generated the indication of the episode type during treatment of the patient. In other words, the medical device may analyze the EGM signal data as it is collected to detect the episode and deliver corresponding treatment in some examples. The medical device may store an indication of the episode type as part of the EGM signal data or in an associated data set, and EGM summary module 130 may identify the episode type from this stored indication. Alternatively, EGM summary module 130 may identify the episode type by analyzing the EGM signal data to determine which type of episode occurred in the patient during the time period of the analyze EGM signal data. Example episode types may include a treated VT/VF episode, a monitored VT episode, a VTNS episode, a high-rate VTNS episode, a VT/VF episode with treatment withheld, an SVT episode, a VOS episode, a fast atrial and ventricular rate episode, a treated AT/AF episode, and a monitored AT/AF episode.

If the identified episode type is related to one or more episode subtypes ("YES" branch of block 328), EGM summary module 130 may classify the episode of the EGM signal data as one of the episode subtypes (332). This classification of the episode as one of a plurality of episode subtypes may be performed according to the presence, or absence, of one or more therapies or other events of the episode, e.g., as described above with respect to Tables 2, 3, and 5-14. In response to the classification, EGM summary module 130 may select, based on the classified episode subtype, one or more portions of the EGM signal data to include in the EGM summary (334). Tables 1-14 are illustrations of example decision logic that may be employed by EGM summary module 130, for example, to determine an episode type and/or episode subtype of a set of EGM signal data and determine which one or more portions (e.g., snippets) of the set of EGM signal data to select for the corresponding EGM summary. In this manner, EGM summary module 130 may employ the logic associated with the classified episode type and/or subtype each episode subtype to select one or more portions of the EGM signal data to include in the EGM summary. Once EGM summary module 130 has selected the portions of the EGM signal data, EGM summary module 130 may proceed to block A.

From block A, EGM summary module 130 may proceed with the process to block 336 of FIG. 17B. If any of the selected portions of the EGM signal data have time windows that overlap ("YES" branch of block 336), EGM summary module 130 may be configured to truncate at least one of the overlapping portions to prevent EGM signal data duplication between the two portions (338). In other examples, EGM summary module 130 may not truncate selected portions. Instead, EGM summary module 130 may analyze the EGM signal data for the timing of events such as detection, one or more therapies, and termination and select the portions of the EGM signal data to be non-overlapping based on the events. Such an approach is described in Tables 5-14. If none of the selected portions of the EGM signal data have time windows that overlap ("NO" branch of block 336), EGM summary module 130 may proceed to generate components of the EGM summary.

EGM summary module 130 may then generate the timeline of markers (e.g., from the marker channel data stored by the medical device) for the time period that includes the selected portions of the EGM signal data (340). EGM summary module 130 may also generate an interval summary, or interval plot, for the time period including the selected portions of the EGM signal data (342). EGM summary module 130 may then organize or generate the EGM summary with the selected portions of the EGM signal data and the interval summary above the timeline of markers (334). Example EGM summaries are shown in FIGS. 8 and 10-16.

In response to organizing the EGM summary, EGM summary module 130 may output the EGM summary for display at another device, such as display device 104 controlled by computing device 102 (346). EGM summary module 130 and/or processors 122 may then control network interface 126 to transmit the EGM summary to computing device 102 via network 110 (348). In some examples, EGM summary module 130 may also generate a patient report combining two or more EGM summaries prior to transmitting the patient report to computing device 102.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory that is tangible. The computer-readable storage media may be referred to as non-transitory. A programmer, such as patient programmer or clinician programmer, or other computing device may also contain a more portable removable memory type to enable easy data transfer or offline data analysis.

The techniques described in this disclosure, including those attributed to server 112 and computing device 102, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, remote servers, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. For example, any of the techniques or processes described herein may be performed within one device or at least partially distributed amongst two or more devices, such as between computing device 102 and server 112. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described herein. Any combination of the described operations or functions is contemplated. These and other examples are within the scope of the following claims.

What is claimed is:

1. A system comprising:
one or more processors configured to:
receive cardiac electrogram (EGM) signal data collected from a medical device associated with a patient, wherein the EGM signal data is representative of a detected single cardiac episode identified as one of a plurality of episode types;
select, based on the identified one of the plurality of episode types, a plurality of non-overlapping portions of the EGM signal data associated with the detected single cardiac episode, wherein the identified episode type of the plurality of episode types is associated with a respective selection of portions of the EGM signal data, and wherein at least two non-overlapping portions of the plurality of the non-overlapping portions of the EGM signal data are discontinuous non-overlapping portions; and
output, for display, the selected plurality of non-overlapping portions of the EGM signal data as an episode summary for the detected single cardiac episode, the episode summary comprising each non-overlapping portion of the EGM signal data of the plurality of non-overlapping portions of the EGM signal data arranged in chronological order.

2. The system of claim 1, wherein the plurality of episode types comprise at least two of a treated ventricular tachycardia/ventricular fibrillation (VT/VF) episode, a monitored VT episode, a non-sustained ventricular tachycardia (VTNS) episode, a high-rate non-sustained ventricular tachycardia (VTNS) episode, a VT/VF episode with treatment withheld, a supraventricular tachycardia (SVT) episode, a ventricular oversensing (VOS) episode, a fast atrial and ventricular rate episode, a treated atrial tachycardia/atrial fibrillation (AT/AF) episode, and a monitored AT/AF episode.

3. The system of claim 1, wherein each episode type of the plurality of episode types is associated with a respective one or more episode subtypes, and wherein the one or more processors are configured to:
classify the detected cardiac episode as one of the respective one or more episode subtypes; and
select, based on the classified one of the respective one or more episode subtypes, the plurality of non-overlapping portions of the EGM signal data, wherein the different episode subtypes are associated with different selections of portions of the EGM signal data.

4. The system of claim 3, wherein the one or more processors are configured to, for each of the plurality of non-overlapping portions of the EGM signal data, determine, based on the classified one of the respective one or more episode subtypes, a time length of the respective portion of the EGM signal data.

5. The system of claim 1, wherein the detected cardiac episode is previously identified by the medical device as the one identified episode type of the plurality of episode types.

6. The system of claim 1, wherein the one or more processors are configured to identify, based on one or more signal characteristics, the detected cardiac episode represented by the EGM signal data as one of the plurality of episode types.

7. The system of claim 1, wherein the one or more processors are configured to determine, based on the identified one of the plurality of episode types, a number of the plurality of non-overlapping portions of the EGM signal data to be selected.

8. The system of claim 1, wherein the plurality of non-overlapping portions of the EGM signal data are associated with one or more events associated with the detected cardiac episode, and wherein the one or more events comprise one or more of an onset of the cardiac episode, a medical device detection of the cardiac episode, a delivered therapy, or a termination of the cardiac episode.

9. The system of claim 1, wherein the one or more processors are configured to:
compare time windows for each portion of the respective selection of portions of EGM signal data, wherein the respective time windows indicate a time duration during which the EGM signal data was collected from the patient;
determine that a first time window for a first portion of the respective selection of portions of EGM signal data overlaps with a second time window for a second portion of the respective selection of portions of EGM signal data; and
truncate at least one of the first portion of the respective selection of portions of EGM signal data and the second portion of the respective selection of portions of EGM signal data to prevent the first portion from including EGM signal data from the same time as the second portion.

10. The system of claim 9, wherein the one or more processors are configured to combine the first portion of the respective selection of portions of EGM signal data with the second portion of the respective selection of portions of EGM signal data into a single timewise continuous portion of EGM signal data, the single timewise continuous portion of EGM signal data comprising two or more of the plurality of non-overlapping portions of the EGM signal data.

11. The system of claim 1, wherein the one or more processors are configured to:
generate a timeline of markers, each of the markers indicating the occurrence of one of a respective sensed ventricular contraction or a respective delivered pacing pulse;
generate, based on the EGM signal data, an interval summary indicating at least one of atrial contraction intervals and ventricle contraction intervals;
organize, into the episode summary, the plurality of non-overlapping portions of the EGM signal data and the interval summary above the timeline of markers, wherein the plurality of non-overlapping portions of the EGM signal data are matched to respective times of the timeline of markers, and wherein the interval summary is positioned above a portion of the time of markers corresponding to onset of the cardiac event; and
output, for display, the organized episode summary.

12. The system of claim 1, further comprising:
a network interface configured to transmit, via a network, the selected plurality of non-overlapping portions of the EGM signal data to a computing device for display at a display device controlled by the computing device; and
one or more networked servers that house the one or more processors and the network interface.

13. A non-transitory computer-readable storage medium comprising instructions that, when executed, cause one or more processors to:

receive cardiac electrogram (EGM) signal data collected from a medical device associated with a patient, wherein the EGM signal data is representative of a detected single cardiac episode identified as one of a plurality of episode types;

select, based on the identified one of the plurality of episode types, a plurality of non-overlapping portions of the EGM signal data associated with the detected single cardiac episode, wherein the identified episode type of the plurality of episode types is associated with a respective selection of portions of the EGM signal data, and wherein at least two non-overlapping portions of the plurality of the non-overlapping portions of the EGM signal data are discontinuous non-overlapping portions; and output, for display, the selected plurality of non-overlapping portions of the EGM signal data as an episode summary for the detected single cardiac episode, the episode summary comprising each non-overlapping portion of the EGM signal data of the plurality of non-overlapping portions of the EGM signal data arranged in chronological order.

14. The non-transitory computer-readable storage medium of claim 13, wherein the plurality of episode types comprise at least two of a treated ventricular tachycardia/ventricular fibrillation (VT/VF) episode, a monitored VT episode, a non-sustained ventricular tachycardia (VTNS) episode, a high-rate non-sustained ventricular tachycardia (VTNS) episode, a VT/VF episode with treatment withheld, a supraventricular tachycardia (SVT) episode, a ventricular oversensing (VOS) episode, a fast atrial and ventricular rate episode, a treated atrial tachycardia/atrial fibrillation (AT/AF) episode, and a monitored AT/AF episode.

15. The non-transitory computer-readable storage medium of claim 13, wherein:

each episode type of the plurality of episode types is associated with a respective one or more episode subtypes;

the computer-readable storage medium further comprises instructions that, when executed, cause the one or more processors to classify the detected cardiac episode as one of the respective one or more episode subtypes; and the instructions that, when executed, cause the one or more processors to select the plurality of non-overlapping portions of the EGM signal comprises instructions that, when executed, cause the one or more processors to select, based on the classified one of the respective one or more episode subtypes, the plurality of non-overlapping portions of the EGM signal data, wherein the different episode subtypes are associated with different selections of portions of the EGM signal data.

16. A method comprising:

receiving cardiac electrogram (EGM) signal data collected from a medical device associated with a patient, wherein the EGM signal data is representative of a detected single cardiac episode identified as one of a plurality of episode types;

selecting, by one or more processors and based on the identified one of the plurality of episode types, a plurality of non-overlapping portions of the EGM signal data associated with the detected single cardiac episode, wherein the identified episode type of the plurality of episode types is associated with a respective selection of portions of the EGM signal data, and wherein at least two non-overlapping portions of the plurality of the non-overlapping portions of the EGM signal data are discontinuous non-overlapping portions; and outputting, by the one or more processors and for display, the selected plurality of non-overlapping portions of the EGM signal data as an episode summary for the detected single cardiac episode, the episode summary comprising each non-overlapping portion of the plurality of non-overlapping portions of the EGM signal data arranged in chronological order.

17. The method of claim 16, wherein the plurality of episode types comprise at least two of a treated ventricular tachycardia/ventricular fibrillation (VT/VF) episode, a monitored VT episode, a non-sustained ventricular tachycardia (VTNS) episode, a high-rate non-sustained ventricular tachycardia (VTNS) episode, a VT/VF episode with treatment withheld, a supraventricular tachycardia (SVT) episode, a ventricular oversensing (VOS) episode, a fast atrial and ventricular rate episode, a treated atrial tachycardia/atrial fibrillation (AT/AF) episode, and a monitored AT/AF episode.

18. The method of claim 16, wherein:

each episode type of the plurality of episode types is associated with a respective one or more episode subtypes;

the method further comprises classifying the detected cardiac episode as one of the respective one or more episode subtypes; and selecting the plurality of non-overlapping portions of the EGM signal comprises selecting, based on the classified one of the respective one or more episode subtypes, the plurality of non-overlapping portions of the EGM signal data, wherein the different episode subtypes are associated with different selections of portions of the EGM signal data.

19. The method of claim 18, wherein selecting the plurality of non-overlapping portions of the EGM signal data comprises, for each of the plurality of non-overlapping portions of the EGM signal data, determining, based on the classified one of the respective one or more episode subtypes, a time length of the respective portion of the EGM signal data.

20. The method of claim 16, wherein the medical device previously identified the detected cardiac episode as the one of the plurality of episodes types.

21. The method of claim 16, further comprising identifying, based on one or more signal characteristics, the detected cardiac episode represented by the EGM signal data as one episode type of the plurality of episode types.

22. The method of claim 16, further comprising determining, based on the identified one of the plurality of episode types, a number of the plurality of non-overlapping portions of the EGM signal data to be selected.

23. The method of claim 16, wherein the plurality of non-overlapping portions of the EGM signal data are associated with one or more events associated with the detected cardiac episode, and wherein the one or more events comprise one or more of an onset of the cardiac episode, a medical device detection of the cardiac episode, a delivered therapy, or a termination of the cardiac episode.

24. The method of claim 16, wherein selecting the plurality of non-overlapping portions of the EGM data further comprises:

comparing time windows for each portion of the respective selection of portions of EGM signal data, wherein the respective time windows indicate a time duration during which the EGM signal data was collected from the patient;

determining that a first time window for a first portion of the respective selection of portions of EGM signal data overlaps with a second time window for a second portion of the respective selection of portions of EGM signal data; and truncating at least one of the first portion of the respective selection of portions of EGM signal data and the second portion of the respective selection of portions of EGM signal data to prevent the first portion from including EGM signal data from the same time as the second portion.

25. The method of claim 24, further comprising combining the first portion of the respective selection of portions of EGM signal data with the second portion of the respective selection of portions of EGM signal data into a single timewise continuous portion of EGM signal data, the single timewise continuous portion of EGM signal data comprising two or more non-overlapping portions of the plurality of non-overlapping portions of the EGM signal data.

26. The method of claim 16, further comprising:

generating a timeline of markers, each of the markers indicating the occurrence of one of a respective sensed ventricular contraction or a respective delivered pacing pulse;

generating, based on the EGM signal data, an interval summary indicating at least one of atrial contraction intervals and ventricle contraction intervals;

organizing, into the episode summary, the plurality of non-overlapping portions of the EGM signal data and the interval summary above the timeline of markers, wherein the plurality of non-overlapping portions of the EGM signal data are matched to respective times of the timeline of markers, and wherein the interval summary is positioned above a portion of the time of markers corresponding to onset of the cardiac event; and outputting, for display, the organized episode summary.

27. The method of claim 16, wherein outputting the selected plurality of non-overlapping portions of the EGM signal data comprises transmitting, from a networked server and via a network, the selected plurality of non-overlapping portions of the EGM signal data to a computing device for display at a display device controlled by the computing device.

* * * * *